US012588818B2

(12) United States Patent
Fisker et al.

(10) Patent No.: US 12,588,818 B2
(45) Date of Patent: **\*Mar. 31, 2026**

(54) DETECTION OF A MOVABLE OBJECT WHEN 3D SCANNING A RIGID OBJECT

(71) Applicant: 3SHAPE A/S, Copenhagen K (DK)

(72) Inventors: Rune Fisker, Virum (DK); Michael Vinther, Copenhagen S (DK); Henrik Öjelund, Lyngby (DK)

(73) Assignee: 3SHAPE A/S, Kobenhavn K (DK)

( \* ) Notice: Subject to any disclaimer, the term of this patent is extended or adjusted under 35 U.S.C. 154(b) by 0 days.

This patent is subject to a terminal disclaimer.

(21) Appl. No.: 18/884,185

(22) Filed: Sep. 13, 2024

(65) Prior Publication Data

US 2025/0143575 A1     May 8, 2025

Related U.S. Application Data

(63) Continuation of application No. 16/018,827, filed on Jun. 26, 2018, now Pat. No. 12,121,319, which is a (Continued)

(30) Foreign Application Priority Data

Jul. 15, 2011     (DK) ........................... PA 2011 00547

(51) Int. Cl.
G06T 7/55          (2017.01)
A61B 5/00          (2006.01)
A61C 19/04         (2006.01)

(52) U.S. Cl.
CPC .......... A61B 5/0062 (2013.01); A61B 5/0088 (2013.01); A61C 19/04 (2013.01); G06T 7/55 (2017.01); G06T 2200/04 (2013.01)

(58) Field of Classification Search
None
See application file for complete search history.

(56) References Cited

U.S. PATENT DOCUMENTS 4,629,324 A     12/1986     Stern et al.
4,965,442 A     10/1990     Girod et al.
(Continued)

FOREIGN PATENT DOCUMENTS

CN          101147688 A          3/2008
CN          102008282 A          4/2011
(Continued)

OTHER PUBLICATIONS

3Shape TRIOS: Frequently Asked Questions FAX, Available online at <http://www.argencanada .com/3shape-trios-frequently-askedquestions-faq>, Nov. 20, 2017, 6 pages.

(Continued)

*Primary Examiner* — Hung Q Dang
(74) *Attorney, Agent, or Firm* — BUCHANAN INGERSOLL & ROONEY PC

(57)          ABSTRACT

Detecting a movable object in a location includes providing a first 3D representation of at least part of a surface; providing a second 3D representation of at least part of the surface; determining for the first 3D representation a first excluded volume in space where no surface can be present; determining for the second 3D representation a second excluded volume in space where no surface can be present; if a portion of the surface in the first 3D representation is located in space in the second excluded volume, the portion of the surface in the first 3D representation is disregarded in the generation of the virtual 3D model, and/or if a portion of the surface in the second 3D representation is located in space in the first excluded volume, the portion of the surface (Continued)

in the second 3D representation is disregarded in the generation of the virtual 3D model.

9 Claims, 19 Drawing Sheets

Related U.S. Application Data continuation of application No. 15/469,009, filed on Mar. 24, 2017, now Pat. No. 10,064,553, which is a continuation of application No. 14/232,363, filed as application No. PCT/EP2012/063687 on Jul. 12, 2012, now Pat. No. 9,629,551.

(60) Provisional application No. 61/508,314, filed on Jul. 15, 2011.

(56) References Cited

U.S. PATENT DOCUMENTS

| | | | |
|---|---|---|---|
| 5,278,983 A | 1/1994 | Kawabe et al. |
| 5,604,817 A | 2/1997 | Massen et al. |
| 5,606,627 A | 2/1997 | Kuo |
| 6,026,189 A | 2/2000 | Greenspan |
| 6,249,600 B1 | 6/2001 | Reed et al. |
| 6,259,452 B1 | 7/2001 | Coorg et al. |
| 6,263,234 B1 | 7/2001 | Engelhardt et al. |
| 6,334,853 B1 | 1/2002 | Kopelman et al. |
| 6,476,803 B1 | 11/2002 | Zhang et al. |
| 6,750,873 B1 | 6/2004 | Rushmeier et al. |
| 6,865,289 B1 | 3/2005 | Berestov |
| 6,904,159 B2 | 6/2005 | Porikli |
| 6,920,415 B1 | 7/2005 | Litke et al. |
| 6,990,228 B1 | 1/2006 | Wiles et al. |
| 7,027,642 B2 | 4/2006 | Rubbert et al. |
| 7,079,679 B2 | 7/2006 | Kirk et al. |
| 7,123,760 B2 | 10/2006 | Mullick et al. |
| 7,197,179 B2 | 3/2007 | Rubbert et al. |
| 7,471,821 B2 | 12/2008 | Rubbert et al. |
| 7,483,062 B2 | 1/2009 | Allman et al. |
| 7,605,817 B2 | 10/2009 | Zhang et al. |
| 7,609,875 B2 | 10/2009 | Liu et al. |
| 7,940,260 B2 | 5/2011 | Kriveshko |
| 8,078,006 B1 | 12/2011 | Sandrew et al. |
| 8,090,194 B2 | 1/2012 | Gordon et al. |
| 8,103,134 B2 | 1/2012 | Sorek et al. |
| 8,121,351 B2 | 2/2012 | Katz et al. |
| 8,260,539 B2 | 9/2012 | Zeng |
| 8,345,961 B2 | 1/2013 | Li et al. |
| 8,526,700 B2 | 9/2013 | Isaacs |
| 8,547,374 B1 | 10/2013 | Sadjadi et al. |
| 8,564,657 B2 | 10/2013 | Michalke et al. |
| 8,743,114 B2 | 6/2014 | Kim et al. |
| 8,867,820 B2 | 10/2014 | Peeper et al. |
| 8,897,526 B2 | 11/2014 | Macleod et al. |
| 9,185,388 B2 | 11/2015 | Mcnamer et al. |
| 9,208,612 B2 | 12/2015 | Frahm et al. |
| 9,299,192 B2 | 3/2016 | Kopelman |
| 9,322,646 B2 | 4/2016 | Pochiraju et al. |
| 9,629,551 B2 | 4/2017 | Fisker et al. |
| 10,064,553 B2 | 9/2018 | Fisker et al. |
| 2002/0006217 A1 | 1/2002 | Rubbert et al. |
| 2004/0125103 A1 | 7/2004 | Kaufman et al. |
| 2004/0125381 A1 | 7/2004 | Chen et al. |
| 2004/0155975 A1 | 8/2004 | Hart et al. |
| 2005/0089213 A1 | 4/2005 | Geng |
| 2005/0090749 A1 | 4/2005 | Rubbert |
| 2005/0105828 A1 | 5/2005 | Oosawa |
| 2005/0142517 A1 | 6/2005 | Frysh et al. |
| 2005/0212753 A1 | 9/2005 | Marvit et al. |
| 2005/0232509 A1 | 10/2005 | Blake et al. |
| 2005/0271996 A1 | 12/2005 | Sporbert et al. |
| 2005/0283065 A1 | 12/2005 | Babayoff |
| 2005/0287490 A1 | 12/2005 | Stookey et al. |
| 2006/0215903 A1 | 9/2006 | Nishiyama |
| 2007/0171220 A1 | 7/2007 | Kriveshko |
| 2007/0207441 A1 | 9/2007 | Lauren et al. |
| 2007/0263924 A1 | 11/2007 | Kochi et al. |
| 2007/0270705 A1 | 11/2007 | Starks |
| 2008/0024768 A1 | 1/2008 | Babayoff |
| 2009/0087050 A1 | 4/2009 | Gandyra |
| 2009/0103103 A1 | 4/2009 | Berner |
| 2009/0104585 A1 | 4/2009 | Diangelo et al. |
| 2009/0160858 A1 | 6/2009 | Chen et al. |
| 2009/0220916 A1 | 9/2009 | Fisker et al. |
| 2009/0279103 A1 | 11/2009 | Thiel et al. |
| 2009/0316966 A1 | 12/2009 | Marshall et al. |
| 2010/0020076 A1 | 1/2010 | Hashima |
| 2010/0156901 A1 | 6/2010 | Park et al. |
| 2010/0239136 A1 | 9/2010 | Gandyra et al. |
| 2010/0240001 A1 | 9/2010 | Steger |
| 2010/0332196 A1 | 12/2010 | Fisker et al. |
| 2011/0004331 A1 | 1/2011 | Cinader et al. |
| 2011/0050848 A1 | 3/2011 | Rohaly et al. |
| 2011/0200249 A1 | 8/2011 | Minear et al. |
| 2011/0228167 A1 | 9/2011 | Sasaki |
| 2011/0310449 A1 | 12/2011 | Kim et al. |
| 2012/0015316 A1 | 1/2012 | Sachdeva et al. |
| 2012/0141949 A1 | 6/2012 | Bodony et al. |
| 2012/0195471 A1 | 8/2012 | Newcombe et al. |
| 2012/0275706 A1 | 11/2012 | Lesellier |
| 2012/0306876 A1 | 12/2012 | Shotton et al. |
| 2013/0002670 A1 | 1/2013 | Kikuta et al. |
| 2013/0113802 A1 | 5/2013 | Weersink et al. |
| 2013/0335417 A1 | 12/2013 | McQueston et al. |
| 2014/0212832 A1 | 7/2014 | Fisker et al. |
| 2014/0255878 A1 | 9/2014 | Jesenko et al. |
| 2018/0049641 A1 | 2/2018 | Fisker et al. |
| 2018/0360317 A1 | 12/2018 | Fisker et al. |

FOREIGN PATENT DOCUMENTS

| | | |
|---|---|---|
| CN | 102055996 A | 5/2011 |
| CN | 102106741 A | 6/2011 |
| DE | 102007005726 A1 | 8/2008 |
| EP | 1607041 A2 | 12/2005 |
| EP | 1607041 A3 | 2/2006 |
| EP | 1607041 B1 | 1/2008 |
| JP | H06154251 A | 6/1994 |
| JP | 2001501049 A | 1/2001 |
| JP | 2001119723 A | 4/2001 |
| JP | 2009523547 A | 6/2009 |
| JP | 2009238245 A | 10/2009 |
| WO | 9701111 A2 | 1/1997 |
| WO | 0180761 A2 | 11/2001 |
| WO | 02076327 A1 | 10/2002 |
| WO | 2008092791 A1 | 8/2008 |
| WO | 2010145669 A1 | 12/2010 |
| WO | 2011047731 A1 | 4/2011 |
| WO | 2011120526 A1 | 10/2011 |
| WO | 2012115862 A2 | 8/2012 |

OTHER PUBLICATIONS

3Shape TRIOS® User Manual, Trios-2013-1-1.2.1.1-B-EN, 77 pages.

*Align Technology, Inc., Petitioner* v. *3Shape A/S Patent Owner,* Case IPR2018-00195—U.S. Pat. No. 9,629,551, Petition for Inter Partes Review, filed with the Patent Trial and Appeal Board, Nov. 21, 2017, 81 pages.

*Align Technology, Inc., Petitioner* v. *3Shape A/S Patent Owner,* Case I PR2018-00196—U.S. Pat. No. 9,629,551, Petition for Inter Partes Review, filed with the Patent Trial and Appeal Board, Nov. 21, 2017, 87 pages.

*Align Technology, Inc., Petitioner* v. *3Shape A/S Patent Owner,* Case I PR2018-00196—U.S. Pat. No. 9,629,551, Declaration of Dr. Chandrajit L. Bajaj, Ph.D. In Support of Inter Partes Review of U.S. Pat. No. 9,629,551, dated Nov. 21, 2017, 106 pages.

*Align Technology, Inc., Petitioner* v. *3Shape A/S Patent Owner,* Case IPR2018-00195—U.S. Pat. No. 9,629,551, Declaration of Dr. Chandrajit L. Bajaj, Ph.D. In Support of Inter Partes Review of U.S. Pat. No. 9,629,551, dated Nov. 21, 2017, 144 pages.

(56)          References Cited

OTHER PUBLICATIONS

*Align Technology, Inc., Petitioner* v. *3Shape A/S Patent Owner*, Case IPR2018-00196—U.S. Pat. No. 9,629,551, Decision Denying Institution of Inter Panes Review, May 24, 2018, 12 pages.
*Align Technology, Inc., Petitioner* v. *3Shape A/S Patent Owner*, Case IPR2018-00195—U.S. Pat. No. 9,629,551, Decision Denying Institution of Inter Partes Review, May 24, 2018, 15 pages.
Baheti, et al., "Intra-oral Scanners: A New Eye in Dentistry", Austin Journal of Orthopedics and Rheumatology, vol. 2, Issue 3, 2015, 7 pages.
Bernardini, et al., "High-Quality Texture Reconstruction from Multiple Scans", IEEE Transactions on Visualization and Computer Graphics, vol. 7, No. 4, Oct.-Dec. 2001, pp. 318-332.
Besl, et al., "A Method for Registration of 3-D Shapes", IEEE Transactions on Pattern Analysis and Machine Intelligence, vol. 14, No. 2, IEEE, XP000248481, Feb. 1992, pp. 239-256.
Broadbent, B. Holly, "A New X-Ray Technique and Its Application to Orthodontia", The Angle Orthodontist, vol. 1, No. 2, Apr. 1931, pp. 45-66, The Angle Society, USA.
Broadhurst, et al., "A Probabilistic Framework for Space Carving", Proceedings Eighth IEEE International Conference on Computer Vision, vol. 1, 2001, 6 pages.
Certified Copy of Priority Document of U.S. Appl. No. 61/445,499, filed Feb. 22, 2011, 51 pages.
Chen, et al., "A Volumetric Stereo Matching Method: Application to Image-Based Modeling", IEEE Computer Society Conference on Computer Vision and Pattern Recognition (Cat. No PR00149) vol. 1, 1999, 6 pages.
*Curriculum Vitae*, Chandrajit L. Bajaj, Ph.D., 49 pages.
Defendant Align Technology, Inc.'s Initial Invalidity Contentions, *3Shape A/S* v. *Align Technology, Inc.*, C.A. No. 1:18-cv-00886-LPS, Aug. 21, 2019, 393 pages.
Dentistry Application of CAD/CAM System, Dentistry Artisan, vol. 21, No. 10, Oct. 1, 1993, 11 pages.
Eisert, et al., "Automatic Reconstruction of Stationary 3-D Objects from Multiple Uncalibrated Camera Views", IEEE Transactions On Circuits and Systems for Video Technology, vol. 10, No. 2, Mar. 2000, pp. 261-277.
Eisert, et al., "Multi-Hypothesis, Volumetric Reconstruction Of 3D Objects From Multiple Calibrated Camera Views", CASSP'99, Phoenix, USA, Mar. 1999, pp. 3509-3512.
Eisert, Peter, "Reconstruction of Volumetric 3D Models", 3D Video Communication: Algorithms, Concepts and Real-Time Systems in Human Centred Communication, John Wiley & Sons, Ltd., 2001, pp. 1-20.
European Office Action issued on Nov. 14, 2014, by European Patent Office in corresponding European Patent Application No. 12745418.9, 8 pages.
File History of U.S. Pat. No. 9,245,374 B2, issued Jan. 26, 2016, 293 pages.
File History of U.S. Pat. No. 9,629,551 B2, issued Apr. 25, 2017, 616 pages.
Fisher, et al., "Dictionary of Computer Vision & Image Processing", Wiley, Second Edition, 2014, 386 pages.
Forne, Christopher J, "3-D Scene Reconstruction From Multiple Photometric Images", PhD Thesis in Electrical and Computer Engineering at the University of Canterbury, Christchurch, New Zealand, Apr. 30, 2007, 179 pages.
Franco, et al., "Efficient Polyhedral Modeling from Silhouettes", IEEE Transactions on Pattern Analysis and Machine Intelligence, vol. 31, No. 3, Mar. 2009, pp. 414-427.
Gehrung, et al., "An Approach to Extract Moving Objects From MLS Data Using a Volumetric Background Representation", ISPRS Annals of the Photogrammetry, Remote Sensing and Spatial Information Sciences, vol. IV-1/W1, Jun. 2017, pp. 107-114.
Grant, et al. , "Glossary of Digital Dental Terms: American College of Prosthodontists", Journal of Prosthodontics, vol. 25, Suppl. 2, Oct. 2016, pp. S2-S9.

Guan, et al., "Multi-view Occlusion Reasoning for Probabilistic Silhouette-Based Dynamic Scene Reconstruction", International Journal of Computer Vision, vol. 90, 2010, pp. 283-303.
Hajeer, et al., "Current Products and Practices Applications of 3D imaging in orthodontics: Part II", Journal of Orthodontics, vol. 31, 2004, pp. 154-162.
Havemann, et al., "Seven Research Challenges of Generalized 3D Documents", IEEE Computer Graphics and Applications, vol. 27, No. 3, May-Jun. 2007, pp. 70-76.
International Search Report (PCT/ISA/210) mailed on Sep. 21, 2012, by the European Patent Office as the International Searching Authority for International Application No. PCT/EP2012/063687, 2 pages.
Ireland, et al., "3D Surface Imaging in Dentistry—What We are Looking At", British Dental Journal, vol. 205, No. 7, Oct. 11, 2008, pp. 387-392.
Jahne, et al., "Handbook of Computer Vision and Applications", Sensors and Imaging, vol. 1, Academic Press, 1999, 657 pages.
Jahne, et al. , "Handbook of Computer Vision and Applications", System and Applications, vol. 3, Academic Press, 1999, 955 pages.
Jahne, et al., "Handbook of Computer Vision and Applications", Signal Processing and Pattern Recognition, Academic Press, vol. 2, 1999, 967 pages.
Jethwa, Manish, "Efficient Volumetric Reconstruction from Multiple Calibrated Cameras", PhD Thesis in Electrical Engineering and Computer Science at MIT, Sep. 2004, 143 pages.
Karatas, et al., "Three-dimensional imaging techniques: A literature review", European Journal of Dentistry, vol. 8, Issue 1, Jan.-Mar. 2014, pp. 132-140.
Koch, et al., "Automatic 3D Model Acquisition from Uncalibrated Image Sequences", IEEE, 1998, pp. 597-604.
Kuhn, et al., "Multi-View Reconstruction of Unknowns Objects within a Known Environment", Advances in Visual Computing, Springer Berlin Heidelberg, Nov. 30, 2009, pp. 784-795.
Kutulakos, et al., "A Theory of Shape by Space Carving", International Journal of Computer Vision, vol. 38, No. 3, pp. 199-218.
Levin, et al., "Modern Dental CAD CAM Systems with Intraoral 3D Profilometers", Measurement Techniques, vol. 53, No. 3, Jul. 2010, pp. 321-324.
Li, et al., "Empty Space Skipping and Occlusion Clipping for Texture-based Volume Rendering", IEEE Visualization, 2003, 8 pages.
Litomisky, et al., "Removing Moving Objects from Point Cloud Scenes", Advances in Depth Image Analysis and Applications, Jan. 2013, pp. 1-10.
Liu, et al., "A Complete Statistical Inverse Ray Tracing Approach to Multi-View Stereo", In CVPR, IEEE, 2011, pp. 913-920.
Logozzo, et al., "A Comparative Analysis of Intraoral 3d Digital Scanners For Restorative Dentistry", The Internet Journal of Medical Technology, vol. 5, No. 1, pp. 1-12.
Lovi, David Israel, "Incremental Free-Space Carving for Real-Time 3D Reconstruction", Master of Science Thesis in Computer Science at University of Alberta, 2011, 74 pages.
Mehl, et al., "Accuracy Testing of a New Intraoral 3D Camera", International Journal of Computerized Dentistry, vol. 12, No. 1, pp. 11-28.
NextEngine TM User's Guide, Oct. 29, 2009.
Niederost, et al., "Automatic 3D Reconstruction and Visualization of Microscopic Objects from a Monoscopic Multifocus Image Sequence", Conference Paper, ETHzurich Research Collection, International Archives of the Photogrammetry, Remote Sensing and Spatial Information Sciences, vol. XXXIV-5/W10, 9 pages.
Notice of Opposition issued on Sep. 3, 2020, by the European Patent Office in corresponding European Patent No. 3401876, 38 pages.
Notice of Opposition issued on Sep. 1, 2021, by the European Patent Office in corresponding European Patent No. 3401876, 36 pages.
Nitschke, et al., "Real-Time Space Carving Using Graphics Hardware", IEICE Transactions on Information and Systems, Aug. 2007, pp. 1175-1184 (11 pages).
Noguchi, et al. , "Microscopic Shape from Focus Using a Projected Illumination Pattern", Mathematical and Computer Modelling, vol. 24, No. 5/6, 1996, pp. 31-48.

(56) References Cited

OTHER PUBLICATIONS

Paris, et al., "A Surface Reconstruction Method using Global Graph Cut Optimization", International Journal of Computer Vision, vol. 66, No. 2, 2010, pp. 141-161.

Pollard, et al., "Change Detection in a 3-D World", IEEE Conference on Computer Vision and Pattern Recognition, Jun. 1, 2007, 6 pages.

Pulli, Kari, "Surface Reconstruction and Display from Range and Color Data", A Dissertation, UMI No. 9819292, 141 pages.

Pulli, et al., "View-based Rendering: Visualizing Real Objects From Scanned Range and Color Data", Rendering Techniques'97, Springer, Vienna, 1997, 12 pages.

Remondino, et al., "Image-Based 3D Modelling: A Review", The Photogrammetric Record, vol. 21, Issue 115, Sep. 2006, pp. 269-291.

Savarese, et al., "3D Reconstruction by Shadow Carving: Theory and Practical Evaluation", International Journal of Computer Vision, vol. 71, No. 3, Mar. 2007, pp. 1-48.

Search Report mailed on Feb. 22, 2012 for the corresponding Danish patent application No. PA 201100547, 1 page.

Search Report mailed on Jun. 9, 2016, for the corresponding Japanese Patent Application No. 2014-519561, 30 pages including 18 pages of English translation.

Sirona The Dental Company Cerec 3D, Operator's Manual Software version 3.6X, Sirena Dental Systems GmbH, Printed in Germany, Mar. 2009, 190 pages.

Slabaugh, et al., "Methods for Volumetric Reconstruction of Visual Scenes", International Journal of Computer Vision, vol. 57, 2004, pp. 179-199 (21 pages).

Slabaugh, Gregory Gibran, "Novel Volumetric Scene Reconstruction Methods for New View Synthesis", PHD Thesis in Electrical and Computer Engineering at Georgia Institute of Technology, Nov. 2002, 209 pages.

Summons to Attend Oral Hearing issued in corresponding European Patent Application No. 18178676.5, dated Apr. 30, 2020, 15 pages.

Tang, et al., "Automatic Reconstruction of as-built Building Information Models from Laser-Scanned Point Clouds: A Review of Related Techniques", Automation in Construction, vol. 19, No. 7, Nov. 1, 2010, pp. 829-843.

Tsukizawa, et al., "3D Digitization of a Hand-held Object with a Wearable Vision Sensor", International Workshop on Computer Vision in Human-Computer Interaction, CVHCI 2004: Computer Vision in Human-Computer Interaction, 2004, pp. 129-141 (11 pages).

Vedula, et al., "Shape and Motion Carving in 6D", Proceedings of the IEEE Conference on Computer Vision and Pattern Recognition, 2000, pp. 1-7.

Wangsiripitak, et al., "Avoiding moving outliers in visual SLAM by Tracking Moving Objects", IEEE International Conference on Robotics and Automation, 2009, 6 pages.

Xiao, et al., "Efficient Partial-Surface Registration for 3D Objects", Computer Vision and Image Understanding, vol. 98, No. 2, 2005, pp. 271-294.

Yamany, et al., "Free-Form Surface Registration Using Surface Signatures", Proceedings of the Seventh IEEE International Conference on Computer Vision, vol. 2, Sep. 20, 1999, pp. 1098-1104.

Yang, et al., "Dealing with Textureless Regions and Specular Highlights-A Progressive Space Carving Scheme Using a Novel Photo-Consistency Measure", Proceedings of the Ninth IEEE International Conference on Computer Vision (ICCV 2003) 2-Volume Set, 2003, 9 pages.

Yuan, et al. , "Inferring 3D Volumetric Shape of Both Moving Objects and Static Background Observed by a Moving Camera", IEEE Conference on Computer Vision and Pattern Recognition, 2007, 8 pages.

Zhu, et al., "Content-Based 3D Mosaics for Dynamic Urban Scenes", Proceedings of SPIE, Defense & Security, vol. 6229, 2006, 13 pages.

Zhu, et al., "Content-Based 3D Mosaic Representation for Video of Dynamic 30 Scenes", Proceedings of the 34th Applied Imagery and Pattern Recognition Workshop, Oct. 19, 2005, pp. 198-203.

Providing a first 3D representation — 101

Providing a second 3D representation — 102

Determining a first excluded volume — 103

Determining a second excluded volume — 104

Test if portion of surface in 3D representation should be disregarded — 105

411

408

512

512

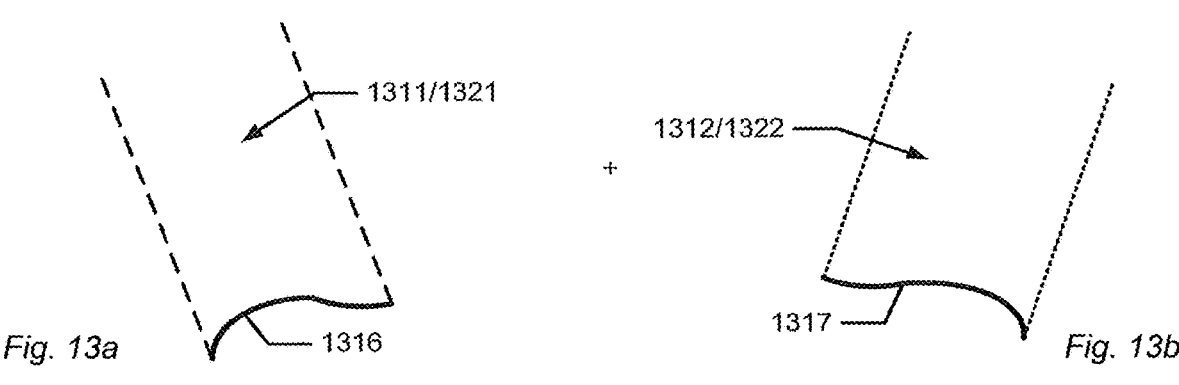
Fig. 13a          Fig. 13b
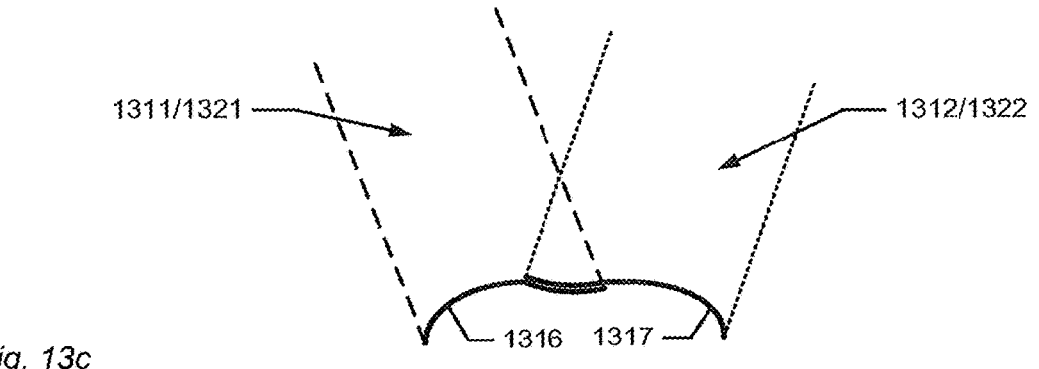
Fig. 13c
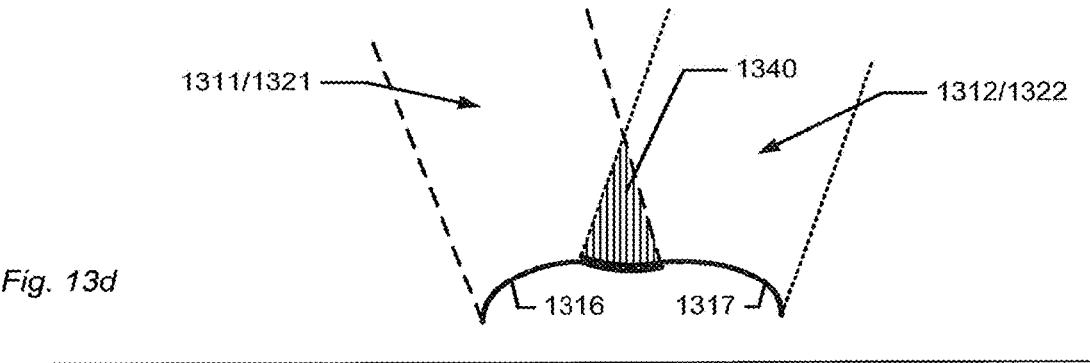
Fig. 13d
Fig. 13e

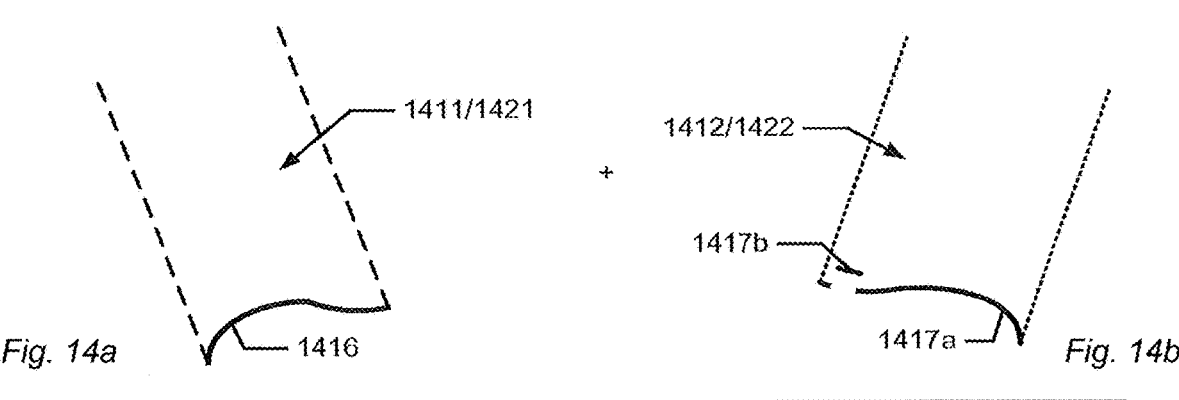
Fig. 14a
Fig. 14b
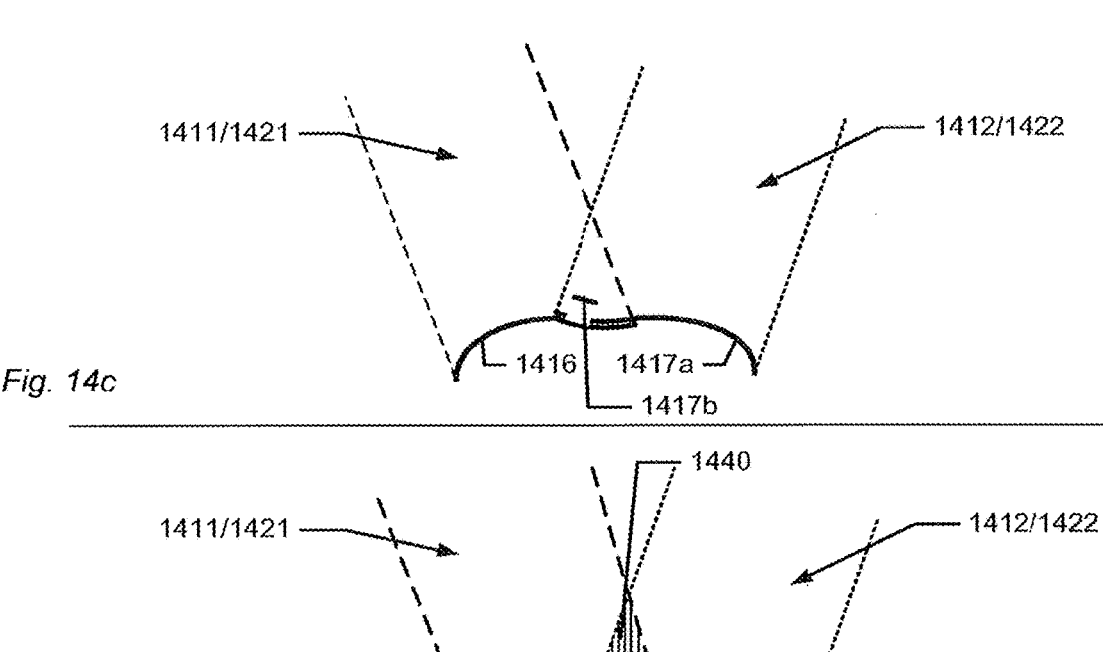
Fig. 14c
Fig. 14d
Fig. 14e

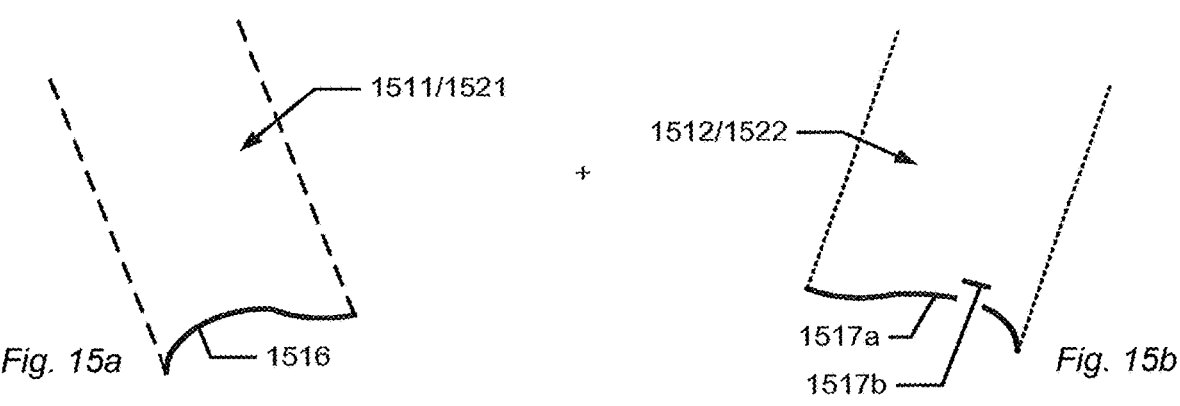
*Fig. 15a*          1516          1512/1522          1517a          1517b          *Fig. 15b*          1511/1521
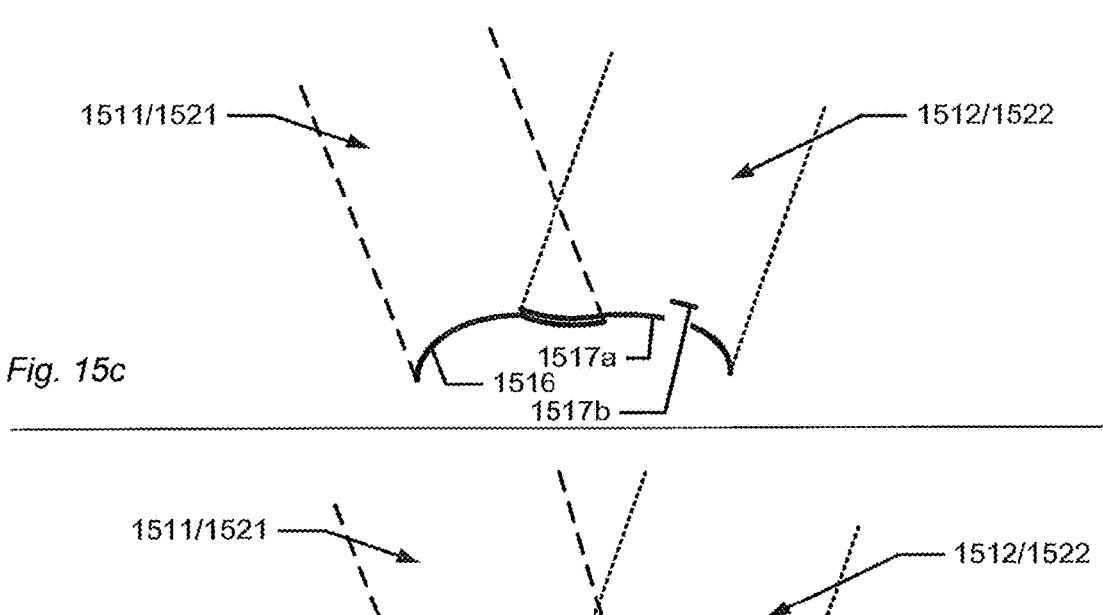
*Fig. 15c*          1511/1521          1512/1522          1517a          1516          1517b
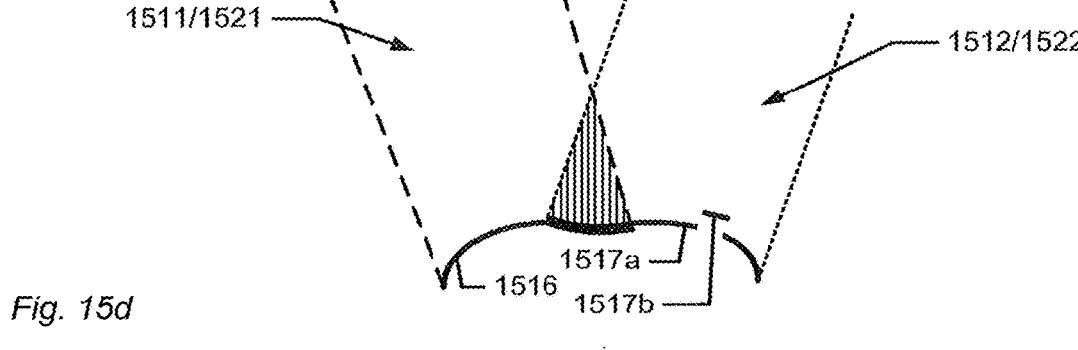
*Fig. 15d*          1511/1521          1512/1522          1517a          1516          1517b
*Fig. 15e*          1519

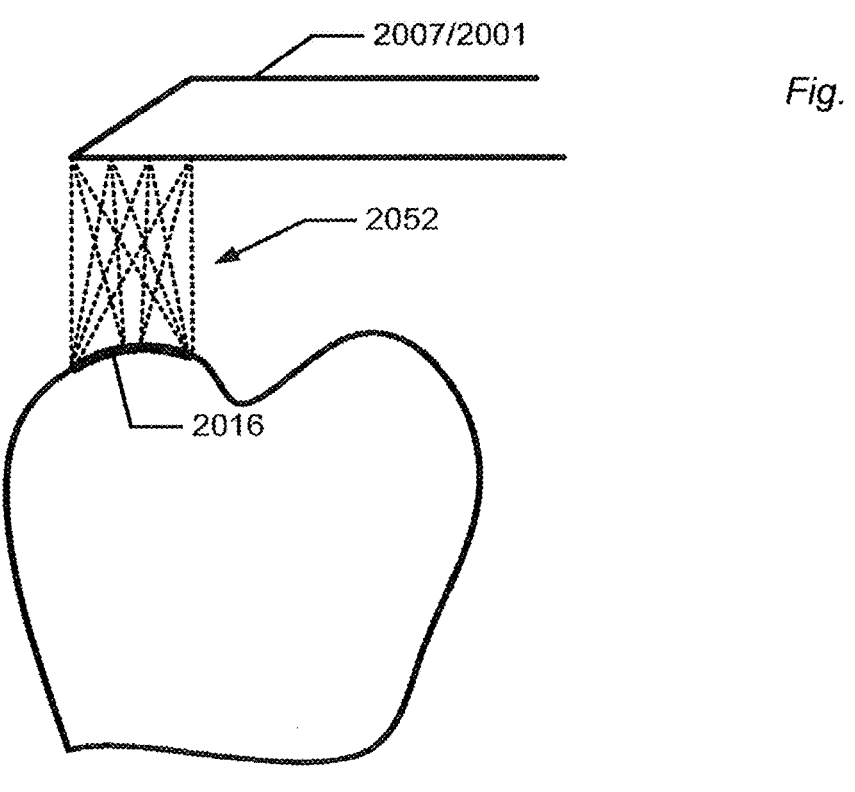
Fig. 20a
Fig. 20b
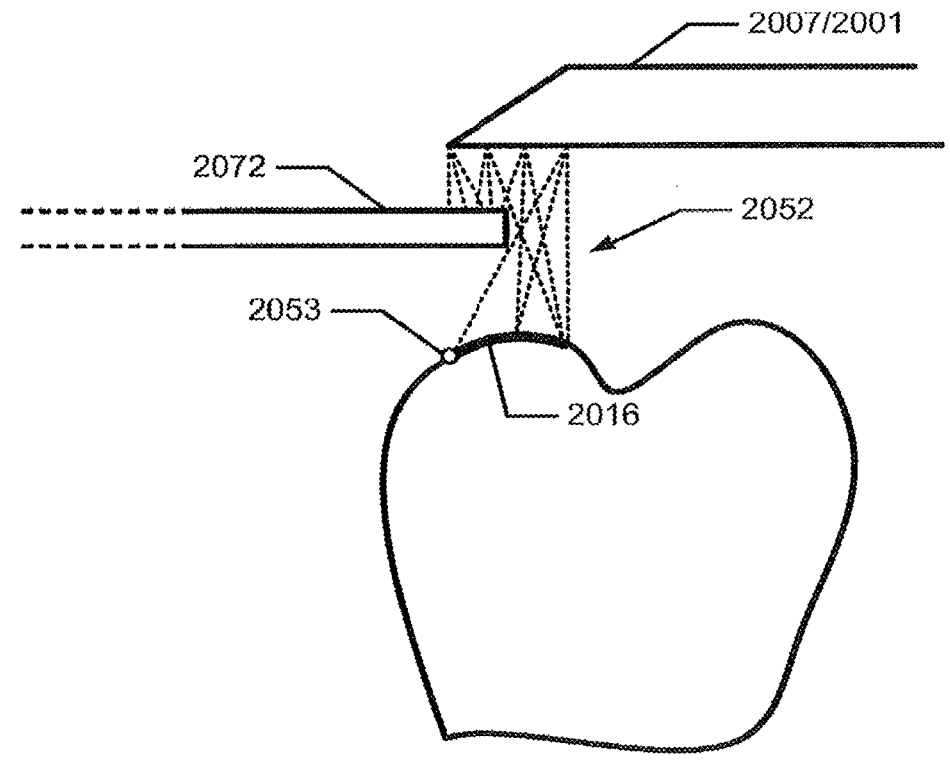

DETECTION OF A MOVABLE OBJECT WHEN 3D SCANNING A RIGID OBJECT

CROSS-REFERENCE TO RELATED APPLICATIONS

The present application is a continuation of U.S. application Ser. No. 16/018,827, filed on Jun. 26, 2018, which is a continuation of U.S. application Ser. No. 15/469,009, filed on Mar. 24, 2017, now U.S. Pat. No. 10,064,553, which is a continuation of U.S. application Ser. No. 14/232,363, filed on Jan. 21, 2014, now U.S. Pat. No. 9,629,551, which is a US National Stage Application of PCT/EP2012/063687, which was filed on Jul. 12, 2012. PCT/EP2012/063687 claims the priority of U.S. Application No. 61/508,314, which was filed on Jul. 15, 2011, and Denmark Application No. PA 2011 00547, which was filed on Jul. 15, 2011. The present application incorporates by reference the subject matter of U.S. application Ser. No. 16/018,827; U.S. application Ser. No. 15/469,009; U.S. application Ser. No. 14/232,363; PCT/EP2012/063687; U.S. Application No. 61/508,314; and Denmark Application No. PA 2011 00547.

FIELD OF THE INVENTION

This invention generally relates to a method for detecting a movable object in a location, when scanning a rigid object in the location by means of a 3D scanner for generating a virtual 3D model of the rigid object. More particularly, the invention relates to scanning of a patient's set of teeth in the mouth of the patient by means of a handheld scanner.

BACKGROUND OF THE INVENTION

In traditional dentistry, the dentist makes a dental impression of the patient's teeth, when the patient needs a crown, a bridge, a denture, a removable, an orthodontic treatment etc. An impression is carried out by placing a viscous liquid material into the mouth, usually in a dental impression tray. The material, usually an alginate, then sets to become an elastic solid, and, when removed from the mouth, provides a detailed and stable reproduction of teeth. When the impression is made, cheek retractors are arranged in the patient's mouth to avoid that the soft movable cheeks affect the impression of the teeth.

Today direct 3D scanning of the patient's teeth can be obtained using an intraoral handheld 3D scanner instead of making a physical dental impression.

When scanning a rigid object in a location for obtaining a virtual 3D model of the rigid object, such as scanning teeth in the mouth of a patient by means of a handheld scanner, it may happen that movable objects such as the patient's cheeks, tongue, or the dentist's instruments or fingers are captured in the sub-scans, because these movable object are located for example between the surface of the teeth and the scanner, whereby the movable object obstruct the view of the teeth for the scanner. As the movable objects are movable they will typically move, and therefore it is likely that the movable object is only captured in one or a few subscans. Since a number of subscans are typically acquired for obtaining a virtual 3D model of, it is likely that there will also be acquired subscans of the same part of the rigid object but without the movable object obstructing the rigid object. Typically the movable objects will move or be moved very fast, since both the patient knows that his tongue should not touch or be near for the teeth when his teeth is scanned and the dentist knows that his instruments should not obstruct the visual access to the teeth. Therefore the movable object will typically only obstruct the visual access of the teeth for a very short time, and this means that the movable object will typically only be captured in one or few subscans. Furthermore, if the dentist notice that a movable object was present when he scanned a part of the teeth, he may return to scan the same part of the teeth where the movable object was before, and thus in most cases, there will also be subscans where the movable object is not present. The problem is then to differentiate between the surface of the movable object and the surface of the rigid object, such that only the surfaces originating from the rigid object are used when generating the virtual 3D model.

In prior art geometry and colour data are used to distinguish between a first and a second tissue, such as hard tissue as teeth and soft tissue as gums, tongue, cheeks, and lips.

EP1607041B discloses a method of providing data useful in procedures associated with the oral cavity characterized by comprising: providing at least two numerical entities ($I_1$, $I_2$, . . . , $I_n$), each said numerical entity representative of the three-dimensional surface geometry and colour of at least part of the intra-oral cavity wherein said numerical entity comprises surface geometry and colour data associated with said part of the intra-oral cavity; wherein at least a portion of said entities ($I_1$, $I_2$, . . . $I_n$) comprise overlapping spatial data, comprising:
  (a) for each entity providing at least one sub entity ($IS'_1$, $IS'_2$, . . . $IS'_n$) comprising a first tissue data set comprising surface geometry and colour data, wherein said colour data thereof is correlated with a colour representative of a first tissue; and
  (b) stitching said first tissue data sets together based on registering portions of said data set comprising said overlapping spatial data ($I_1$, $I_2$, . . . $I_n$) and manipulating said entity to provide desired data therefrom.

Furthermore, in image processing a method called space carving is used for building up a 3D model.

The article "A Method for Registration of 3-D Shapes" by Besl and Mckay, IEEE Transactions of Patten Analysis and Machine Intelligence, vol. 14, no. 2, February 1992 discloses a method for accurate and computationally efficient registration of 3-D shapes.

However, none of the prior art considers the case where some of the objects in the location are movable.

Thus it remains a problem to distinguish between movable objects and rigid objects, when both movable objects and rigid objects are present in a location, when scanning in the location for obtaining a virtual 3D model of the rigid object.

SUMMARY

Disclosed is a method for detecting a movable object in a location, when scanning a rigid object in the location by means of a 3D scanner for generating a virtual 3D model of the rigid object, wherein the method comprises:
  providing a first 3D representation of at least part of a surface by scanning at least part of the location;
  providing a second 3D representation of at least part of the surface by scanning at least part of the location;
  determining for the first 3D representation a first excluded volume in space where no surface can be present;
  determining for the second 3D representation a second excluded volume in space where no surface can be present;

if a portion of the surface in the first 3D representation is located in space in the second excluded volume, the portion of the surface in the first 3D representation is disregarded in the generation of the virtual 3D model, and/or if a portion of the surface in the second 3D representation is located in space in the first excluded volume, the portion of the surface in the second 3D representation is disregarded in the generation of the virtual 3D model.

Consequently, it is an advantage to disregard a surface portion from one representation if the surface portion is located in space in the excluded volume of another representation, because a surface portion detected in an excluded volume represents a movable object which is not part of the rigid object.

Thus it is an advantage that the method provides a determination of whether a detected surface portion is a point in space where there should be no surface, by detecting the space of the surface portion in both a first representation and in the second representation. If the surface portion is only present in one of the representations and the representations cover the same space of the surface portion, then the surface portion must represent an object which was only present when one of the representations were acquired, and therefore the surface portion must originate from a movable object, which has moved during the acquisitions of the two representations.

When scanning a surface, then all space which is not occupied by the surface, may be defined as empty space, and if in a later scan, a surface is detected in the empty space, then that surface is disregarded.

Likewise, if in a later scan, a volume region is seen to be empty, but that volume region was covered by a surface in a previous scan, then the surface is disregarded from the 3D virtual model.

By disregarding is meant not taken into account, such as deleting or not adding, when generating the 3D virtual model. If a surface portion from the first representation has already been added to the virtual 3D model, it may be deleted from it again if it is found that the surface portion is in the second excluded volume. If a surface portion from the second representation is found to be in the first excluded volume, the surface portion is not added to the virtual 3D model.

If a volume region in one representation or subscan is empty then it is excluded from addition of new surfaces even though a later representation or subscan shows that a surface is present in the volume regions. If a later representation or subscan shows that the volume is empty then a surface from a previous subscan in that volume is removed from the 3D model.

A common scan volume can be defined, which is the volume in space where the first scan volume and the second scan volume are overlapping. Thus it may be defined as the volume in space, where all volume units are contained in both the first scan volume and in the second scan volume.

If a portion of the surface in the first 3D representation is not located in space in the second excluded volume, and/or if a portion of the surface in the second 3D representation is not located in space in the first excluded volume, no surface portions are disregarded yet, and the scanning may continue by providing a third representation, a fourth representation etc.

Typically when scanning an object, such as a set of teeth, more representations or subscans may be provided, such as 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000 etc. during a complete scanning process.

In some embodiments the rigid object is a patient's set of teeth, and the location is the mouth of the patient.

In some embodiments the movable object is a soft tissue part of the patient's mouth, such as the inside of a cheek, the tongue, lips, gums and/or loose gingival.

In some embodiments the movable object is a dentist's instrument or remedy which is temporarily present in the patient's mouth, such as a dental suction device, cotton rolls, and/or cotton pads.

In some embodiments the movable object is a finger, such as the dentist's finger or the dental assistant's finger.

In some embodiments the 3D scanner is a scanner configured for acquiring scans of an object's surface for generating a virtual 3D model of the object.

In some embodiments at least part of the surface captured in the first representation and at least part of the surface captured in the second representation are overlapping the same surface part on the rigid object.

In some embodiments the first representation of at least part of the surface is defined as the first representation of at least a first part of the surface, and the second representation of at least part of the surface is defined as the second representation of at least a second part of the surface.

The first part of the surface and the second part of the surface may be two different parts, or may be the same part, or may be partly the same part.

In some embodiments the first part of the surface and the second part of the surface are at least partially overlapping.

In some embodiments the surface is a surface in the location.

In some embodiments the surface is at least part of the surface of the rigid object and/or at least part of the surface of the movable object.

The purpose of scanning is to acquire a virtual 3D model of the rigid object, e.g. teeth, but if there is a movable object in the location, e.g. the mouth of the patient, when scanning, then the movable object may also be captured in some of the subscans.

In some embodiments the method comprises determining a first scan volume in space related to the first representation of at least part of the surface, and determining a second scan volume in space related to the second representation of at least part of the surface.

The scan volume may be the volume in space which is located in front of the captured surface relative to the scanner.

In some embodiments the scan volume is defined by the focusing optics in the 3D scanner and the distance to the surface which is captured.

The scan volume may be defined as the physical volume which the scanner is adapted to scan relative to the view position and the orientation of the scanner, such as relative to the scan head of the scanner.

Furthermore, the scanner comprises a scan head, and the scan volume may be defined as the distance in space between the surface and the scan head times the area of the opening of the scan head. The scan head may comprise the focusing optics of the scanner.

Instead of the area of the opening of the scan head, the area of the surface projected in the optical direction may be considered.

In some embodiments the first scan volume related to the first representation of at least part of the surface is the volume in space between the focusing optics of the 3D scanner and the surface captured in the first representation; and the second scan volume related to the second representation of at least part of the surface is the volume in space between the focusing optics of the 3D scanner and the surface captured in the second representation.

In some embodiments if no surface is captured in at least part of the first or second representation, then the first or second scan volume is the volume in space between the focusing optics of the 3D scanner and the longitudinally extent of the scan volume.

In some embodiments the first excluded volume and the second excluded volume in space where no surface can be present corresponds to the first scan volume and the second scan volume, respectively.

The space between the focusing optics of the 3D scanner and the captured surface must be an empty space, unless a transparent object, which is not detectable by the 3D scanner, was located in the scan volume.

The scan volume may be defined as the maximum volume which can be scanned, e.g. the maximum volume of light which can be transmitted from the scan head. In that case, the excluded volume would only correspond to the scan volume, if the captured surface is located at the end or edge of the scan volume. But in most cases the excluded volume would be smaller than the scan volume, if the definition of the scan volume was the maximum volume.

In some embodiments the volume of the 3D scanner itself is defined as an excluded volume.

In some embodiments the volume of the 3D scanner itself is comprised in the first excluded volume and in the second excluded volume.

In some embodiments a near threshold distance is defined, which determines a distance from the captured surface in the first representation and the second representation, where a surface portion in the second representation or the first representation, respectively, which is located within the near threshold distance from the captured surface and which is located in space in the first excluded volume or in the second excluded volume, respectively, is not disregarded in the generation of the virtual 3D model.

The near threshold defines how far from the representation or surface in a subscan possibly movable objects are disregarded from the generation of the virtual 3D model. The near threshold distance is defined for avoiding that too much of a representation of a surface is incorrectly disregarded, since there may be noise in the representation and since the registration/alignment between representations or sub-scans may not be completely accurate. Due to different levels of noise in different subscans or due to inaccurate registration/alignment of subscans, two subscans of the same surface may incorrectly look like two different surfaces. The near threshold distance may be such as 0.01 mm, 0.05 mm, 0.09 mm, 0.10 mm, 0.15 mm, 0.20 mm etc.

In some embodiments a far threshold distance is defined, which determines a distance from the captured surface, where the volume outside the far threshold distance is not included in the excluded volume of a representation.

Thus the volume outside the far threshold distance is not included in the first excluded volume of the first 3D representation, and the volume outside the far threshold distance is not included in the second excluded volume of the second 3D representation.

According to this embodiment any acquired data or surface or surface points of the first or second representation, which is/are present or located outside the far threshold distance, is not used to determine or define the first or second excluded volume, respectively.

It is an advantage because a surface or surface points from a movable object or from another part of the tooth surface can actually be present outside the far threshold distance without being detected by the scanner, due to the geometry and optical properties of the scanner. The light rays from the scanner head may be transmitted in any directions and with any angle or inclination from a normal plane of the scanner head, and therefore a light ray can be transmitted from the scanner head to a point which is placed behind the movable object or the other part of the tooth surface, when the movable object or the other part of the tooth surface is present partly in front of the scanner head.

Thus the volume outside the far threshold distance is not included in the excluded volume, because in the volume outside the far threshold distance a surface can be present even though no surface is detected by the scanner.

The far threshold distance defines or determines a distance from the captured surface, where the volume or region within the far threshold distance is included in the excluded volume.

Thus if utilizing or applying the far threshold distance, the excluded volume for a representation will be smaller than if not applying the far threshold distance, and therefore less volume can be excluded.

However, the advantage of applying a far threshold distance is that only volumes which can truly be excluded, will be excluded, meaning that the general scan data will have a higher quality.

Thus even though no surface or surface points has/have been detected in a volume or region between the scanner and the tooth surface, the whole region cannot be defined as excluded volume, because the light rays from and to the scanner may travel with inclined angles relative to a normal of the scan head, which means that the scanner can detect a point on the tooth surface even though another part of the tooth is actually placed, at least partly, between the detected tooth surface and the scanner. Therefore a far threshold distance is defined, and no data detected outside this far threshold distance from the tooth surface is used to define the excluded volume of a representation. Only data detected inside the far threshold distance is used to define the excluded volume, because only within this distance can one be certain that the data detected actually corresponds to the real physical situation.

The scanner may detect that no surface is present in the volume or region outside the far threshold distance between the tooth surface and the scanner, but this data or information cannot be used to define the excluded volume of the representation, because there may actually be a movable object or another part of the tooth surface in this region or volume which the scanner overlooks because of its inclined light rays.

Furthermore, the scanner may overlook a surface part even though the surface part is in the scan volume. This can be caused by that the surface part is outside the focus region of the scanner, for example if the surface part is too close to the opening of the scanner head and/or scanner body, as the focus region may begin some distance from the scanner head and/or scanner body. Alternatively and/or additionally this can be caused by the lightning conditions, which may not be optimal for the given material of the surface, whereby the surface is not properly illuminated and thus can become invisible for the scanner. Thus in any case the scanner may overlook or look through the surface part. Hereby a volume in space may erroneously be excluded, since the scanner detects that no surface is present, and therefore a surface portion captured in this excluded volume in another 3D representation or scan would be disregarded. For avoiding that this happens, which would be unfavorably if the surface part was a true tooth surface, the far threshold distance can be defined, such that the excluded volume becomes smaller, such that only volume which really can be excluded is excluded.

It is an advantage that real surface points of a tooth are not erroneously disregarded, whereby fewer holes, i.e. regions with no scan data, are created in the scans. Thus the excluded volume is reduced by means of the far threshold distance for avoiding that too much surface information is incorrectly disregarded.

The light rays from the scan head of the scanner may spread or scatter or disperse in any directions.

Even if an object, such as a movable object, is arranged between the scan head and the surface of a rigid object, e.g. a tooth, the scanner may still capture a surface point on the tooth surface which is present or hidden "under" the object, because of the angled or inclined light rays. A surface point or area may just have to be visible for one or a small number of light rays from and/or to the scanner in order for that surface point or area to be detected.

Since the far threshold distance determines a distance from the captured surface in a representation, where any acquired data or surface or surface points, which is/are present or located outside the far threshold distance, is not used to define the excluded volume of the representation, any acquired data or surface or surface points in the volume between the far threshold distance and the scan head is not included in the definition of the excluded volume. The actual distance of the far threshold may depend or be calculated based on the optics of the scanner. The far threshold distance may be a fixed number, such as about 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. Alternatively, the far threshold distance may be a percentage or a fraction of the length of the scan volume, such as about 20%, 25%, 30%, 35%, 40%, 45%, or 50% of the length of the scan volume, or such as $\frac{1}{2}$, $\frac{1}{3}$, $\frac{1}{4}$, $\frac{1}{5}$ of the length of the scan volume.

The far threshold distance may be based on a determination of how far a distance from a detected point of the surface it is possible to scan, i.e. how much of the surface around a detected point that is visible for the scanner. If the visible distance in one direction from a surface point is short, then the far threshold distance will be smaller than if the distance in all directions from a surface point is long.

In some embodiments the first representation of at least part of a surface is a first subscan of at least part of the location, and the second representation of at least part of the surface is a second subscan of at least part of the location.

In some embodiments the first representation of at least part of a surface is a provisional virtual 3D model comprising the subscans of the location acquired already, and the second representation of at least part of the surface is a second subscan of at least part of the location.

In some embodiments acquired subscans of the location are adapted to be added to the provisional virtual 3D model concurrently with the acquisition of the subscans.

In some embodiments the provisional virtual 3D model is termed as the virtual 3D model, when the scanning of the rigid object is finished.

In some embodiments the method comprises:
provide a third 3D representation of at least part of a surface by scanning at least part of the location;
determine for the third 3D representation a third excluded volume in space where no surface can be present;

if a portion of the surface in the first 3D representation is located in space in the third excluded volume, the portion of the surface in the first 3D representation is disregarded in the generation of the virtual 3D model, and/or
if a portion of the surface in the second 3D representation is located in space in the third excluded volume, the portion of the surface in the second 3D representation is disregarded in the generation of the virtual 3D model, and/or
if a portion of the surface in the third 3D representation is located in space in the first excluded volume and/or in the second excluded volume, the portion of the surface in the third 3D representation is disregarded in the generation of the virtual 3D model.

In some embodiments the provisional virtual 3D model comprises the first representation of at least part of the surface and the second representation of at least part of the surface, and where the third representation of at least part of the surface is added to the provisional virtual 3D model.

Thus the timewise first acquired representation, which is not necessarily the first representation, and the timewise second acquired representation, which is not necessarily the second representation, may be combined to create the provisional virtual 3D model, and each time a new representation is acquired or provided, the new representation may be added to the provisional virtual 3D model, whereby the provisional virtual 3D model grows for each added representation.

In some embodiments the virtual 3D model is used for virtually designing a restoration for one or more of the patient's teeth.

Thus the purpose of scanning is to obtain a virtual 3D model of the patient's teeth. If the patient should have a restoration, e.g. a crown, a bridge, a denture, a partial removable etc., the restoration can be digitally or virtually designed on or relative to the 3D virtual model.

In some embodiments the virtual 3D model is used for virtually planning and designing an orthodontic treatment for the patient.

In some embodiments the relative motion of the scanner and the rigid object is determined.

In some embodiments the relative motion of the scanner and the rigid object is determined by means of motion sensors.

If the scanner used for acquiring the sub-scans is a handheld scanner, then the relative position, orientation or motion of scanner and the object which is scanned must be known. The relative position, orientation and motion of the scanner can be determined by means of position, orientation and/or motion sensors. However, if these sensors are not accurate enough for the purpose, the precise relative position of scanner and object can be determined by comparing the obtained 3D surfaces in the sub-scans, such as by means of alignment/registration.

A motion sensor is a device that can perform motion measurement, such as an accelerometer. Furthermore the motion sensor may be defined as a device which works as a position and orientation sensor as well.

A position sensor is a device that permits position measurement. It can be an absolute position sensor or a relative position sensor, also denoted displacement sensor. Position sensors can be linear or angular.

An orientation sensor is a device that can perform orientation measurement, such as a gyroscope.

In some embodiments the relative motion of the scanner and the rigid object is determined by registering/aligning the first representation and the second representation.

In some embodiments the first representation and the second representation are aligned/registered before the first excluded volume and the second excluded volume are determined.

Thus after the first and the second representation are provided, they may be aligned/registered, and after this, the first and second excluded volume may be determined, and then it is detected whether a portion of the surface in the first 3D representation or in the second 3D representation is located in space in the second excluded volume or in the first excluded volume, respectively, such that such portion of the surface in the representation is disregarded in the generation of the virtual 3D model.

Alignment or registration may comprise bringing the 3D representations or subscans together in a common reference system, and then merging them to create the virtual 3D model or a provisional virtual 3D model. For each representation or subscan which is aligned/registered to the provisional virtual 3D model, the model grows and finally it becomes the virtual 3D model of the object.

In some embodiments the relative motion of the scanner and the rigid object determined by means of the motions sensors is verified and potentially adjusted by registering/aligning the first representation and the second representation.

In some embodiments motion sensors are used for an initial determination of the relative motion of the scanner and the rigid object, and where registering/aligning is used for the final determination of the relative motion of the scanner and the rigid object.

Thus in practice the motion sensors may be used as a first guess for the motion, and based on this the alignment/registration may be used for testing the determined motion and/or determining the precise motion or adjusting the determined motion.

In some embodiments the optical system of the scanner is telecentric.

A telecentric system is an optical system that provides imaging in such a way that the chief rays are parallel to the optical axis of said optical system. In a telecentric system out-of-focus points have substantially same magnification as in-focus points. This may provide an advantage in the data processing. A perfectly telecentric optical system may be difficult to achieve, however an optical system which is substantially telecentric or near telecentric may be provided by careful optical design. Thus, when referring to a telecentric optical system it is to be understood that it may be only near telecentric.

As the chief rays in a telecentric optical system are parallel to the optical axis, the scan volume becomes rectangular or cylindrical.

In some embodiments the optical system of the scanner is perspective.

If the optical system is a perspective system, the chief rays are angled relative to the optical axis, and the scan volume thus becomes cone shaped.

Note that the scan volume is typically a 3D shape.

In some embodiments a mirror in a scan head of the scanner provides that the light rays from the light source in the scanner are transmitted with an angle relative to the opening of the scan head.

The scan volume may be defined not as rectangular but rather as resembling a parallelogram.

The light reflected back from a point on the surface may be projected as rays forming a cone or as parallel rays.

In some embodiments the 3D scanner is a hand-held scanner.

The 3D scanner may for example be a hand-held intraoral scanner.

In some embodiments the scanner is a pinhole scanner.

A pinhole scanner comprises a pinhole camera having a single small aperture. The size of the aperture may be such as $\frac{1}{100}$ or less of the distance between it and the projected image. Furthermore, the pinhole size may be determined by the formula $d=2\sqrt{(2\lambda)}$, where dis pinhole diameter, f is focal length, i.e. the distance from pinhole to image plane, and $\lambda$ is the wavelength of light.

It is an advantage to use the present method for detecting a movable object in a location in a pinhole scanner, since determining the first excluded volume and the second excluded volume is very fast, easy and accurate due to the pinhole setup, where the camera and the light source/ projected pattern, respectively, of the scanner are well-defined points in space relative to the captured surface.

Furthermore, if the scanner is a pinhole scanner, the excluded volume may be bigger, compared to if the scanner is not a pinhole scanner. The reason for this is because no far threshold distance can or should be defined when using a pinhole scanner, since no volume between the scanner and the captured tooth surface may not be included in the excluded volume due to the geometry and optical properties of the scanner. The pinhole scanner cannot overlook a surface or surface points from e.g. a movable object due to its geometry and optical properties.

In some embodiments the scanner comprises an aperture, and the size of the aperture is less than $\frac{1}{100}$ of the distance between it and the projected image.

This size of aperture corresponds to a pinhole scanner.

In some embodiments the scanner comprises an aperture, and the size of the aperture is more than $\frac{1}{100}$ of the distance between it and the projected image.

This size of aperture corresponds to a scanner which is not a pinhole scanner.

FURTHER ASPECTS

According to another aspect of the invention, disclosed is a method for detecting movable objects in the mouth of a patient, when scanning the patient's set of teeth in the mouth by means of a 3D scanner for generating a virtual 3D model of the set of teeth, wherein the method comprises:

providing a first 3D representation of at least part of a surface by scanning at least part of the teeth;

providing a second 3D representation of at least part of the surface by scanning at least part of the teeth;

determining for the first 3D representation a first excluded volume in space where no surface can be present;

determining for the second 3D representation a second excluded volume in space where no surface can be present;

if a portion of the surface in the first 3D representation is located in space in the second excluded volume, the portion of the surface in the first 3D representation is disregarded in the generation of the virtual 3D model, and/or if a portion of the surface in the second 3D representation is located in space in the first excluded volume, the portion of the surface in the second 3D representation is disregarded in the generation of the virtual 3D model.

According to another aspect of the invention, disclosed is a method for detecting a movable object in a location, when scanning a rigid object in the location by means of a 3D scanner for generating a virtual 3D model of the rigid object, wherein the method comprises:

providing a first representation of at least part of a surface by scanning the rigid object;

determining a first scan volume in space related to the first representation of at least part of the surface;

providing a second representation of at least part of the surface by scanning the rigid object;

determining a second scan volume in space related to the second representation of at least part of the surface;

if there is a common scan volume, where the first scan volume and the second scan volume are overlapping, then:

determine whether there is a volume region in the common scan volume which in at least one of the first representation or the second representation is empty and comprises no surface; and if there is a volume region in the common scan volume which in at least one of the first representation or the second representation is empty and comprises no surface, then exclude the volume region by disregarding in the generation of the virtual 3D model any surface portion in the second representation or in the first representation, respectively, which is detected in the excluded volume region, since a surface portion detected in the excluded volume region represents a movable object which is not part of the rigid object.

According to another aspect of the invention, disclosed is a method for detecting a movable object in a location, when scanning a rigid object in the location by means of a 3D scanner for generating a virtual 3D model of the rigid object, wherein the method comprises:

providing a first surface by scanning the rigid object;

determining a first scan volume related to the first surface;

providing a second surface by scanning the rigid object;

determining a second scan volume related to the second surface;

where the first scan volume and the second scan volume are overlapping in an overlapping/common scan volume;

if at least a portion of the first surface and a portion of the second surface are not coincident in the overlapping/common scan volume, then disregard the portion of either the first surface or the second surface in the overlapping/common scan volume which is closest to the focusing optics of the 3D scanner, as this portion of the first surface or second surface represents a movable object which is not part of the rigid object.

According to another aspect of the invention, disclosed is a method for detecting a movable object in the mouth of the patient, when scanning the patient's set of teeth by means of a 3D scanner for generating a virtual 3D model of the set of teeth, wherein the method comprises:

providing a first surface by scanning the set of teeth;

determining a first scan volume related to the first surface;

providing a second surface by scanning the set of teeth;

determining a second scan volume related to the second surface;

where the first scan volume and the second scan volume are overlapping in an overlapping/common scan volume;

if at least a portion of the first surface and a portion of the second surface are not coincident in the overlapping/common scan volume, then disregard the portion of either the first surface or the second surface in the overlapping/common scan volume which is closest to the focusing optics of the 3D scanner, as this portion of the first surface or second surface represents a movable object which is not part of the set of teeth.

According to another aspect of the invention, disclosed is a method for detecting movable objects recorded in subscans, when scanning a set of teeth by means of a scanner for generating a virtual 3D model of the set of teeth, where the virtual 3D model is made up of the already acquired subscans of the surface of the set of teeth, and where new subscans are adapted to be added to the 3D virtual model, when they are acquired, wherein the method comprises:

acquiring at least a first subscan of at least a first surface of part of the set of teeth, where the at least first subscan is defined as the 3D virtual model;

acquiring a first subscan of a first surface of part of the set of teeth;

determining a first scan volume of the first subscan;

determining a scan volume of the virtual 3D model;

if the first scan volume of the first subscan and the scan volume of the virtual 3D model are at least partly overlapping in a common scan volume; then:

calculate whether at least a portion of the first surface lies within the common scan volume;

calculate whether at least a portion of the surface of the virtual 3D model lies within the common scan volume, and determine whether at least a portion of a surface is present in the overlapping volume only in one subscan and not the other subscan/3D virtual model;

if at least a portion of a surface is present in only one subscan, then disregard the portion of the surface in the overlapping volume which is closest to the focusing optics of the scanner, since the portion of the surface represents a movable object which is not part of the set of teeth, and the portion of the surface is disregarded in the creation of the virtual 3D model of the set of teeth.

According to another aspect of the invention, disclosed is s method for detecting movable objects recorded in subscans, when scanning a set of teeth by means of a scanner for generating a virtual 3D model of the set of teeth, wherein the method comprises:

a) providing a first subscan of a first surface of part of the set of teeth;

b) calculating a first scan volume of the first subscan;

c) providing a second subscan of a second surface of part of the set of teeth;

d) calculating a second scan volume of the second subscan; and e) if the first scan volume and the second scan volume are at least partly overlapping in a common scan volume; then:

f) calculate whether at least a portion of the first surface lies within the common scan volume;

g) calculate whether at least a portion of the second surface lies within the common scan volume, and h) if at least a portion of the first surface or at least a portion of the second surface lie within the common scan volume, and the portion of the first surface or the portion of the second surface is located in space between the scanner and at least a portion of the second surface or at least a portion of the first surface, respectively;

then the portion of the surface represents a movable object which is not part of the set of teeth, and the portion of the surface is disregarded in the creation of the virtual 3D model of the set of teeth.

In some embodiments the method above further comprises:

providing a third subscan of a third surface of part of the set of teeth;

calculating a third scan volume of the third subscan;

if the third scan volume is at least partly overlapping with the first scan volume and/or with the second scan volume in a common scan volume; then repeat steps f)-h) for the third subscan with respect to the first subscan and/or the second subscan.

Further embodiments are disclosed in the following sections:

Focus Scanning and Motion Determination

In some embodiments the 3D scanning comprises the steps of:

generating a probe light, transmitting the probe light towards the object thereby illuminating at least a part of the object, transmitting light returned from the object to a camera comprising an array of sensor elements, imaging on the camera at least part of the transmitted light returned from the object to the camera by means of an optical system, varying the position of the focus plane on the object by means of focusing optics, obtaining at least one image from said array of sensor elements, determining the in-focus position(s) of:

each of a plurality of the sensor elements for a sequence of focus plane positions, or each of a plurality of groups of the sensor elements for a sequence of focus plane positions.

There may be for example more than 200 focus plane images, such as 225 focus plane images, in a sequence of focus plane images used in generating a 3D surface. The focus plane images are 2D images.

Image sensor(s), photo sensor and the like can be used for acquiring images in the scanner. By scanning is generally meant optical scanning or imaging using laser light, white light etc.

In some embodiments a sequence of focus plane images are depth images captured along the direction of the optical axis.

In some embodiments at least a part of the object is in focus in at least one of the focus plane images in a sequence of focus plane images.

In some embodiments the time period between acquisition of each focus plane image is fixed/predetermined/known.

Each focus plane image may be acquired a certain time period after the previous focus plane image was acquired. The focus optics may move between the acquisition of each image, and thus each focus plane image may be acquired in a different distance from the object than the previous focus plane images.

One cycle of focus plane image capture may be from when the focus optics is in position P until the focus optics is again in position P. This cycle may be denoted a sweep. There may such as sweeps per second.

A number of 3D surfaces or sub-scans may then be combined to create a full scan of the object for generating a 3D model of the object.

In some embodiments determining the relative motion of the scanner during the acquisition of the sequence of focus plane images is performed by analysis of the sequence in itself.

Motion Detection by Means of Hardware

In some embodiments determining the relative motion of the scanner during the acquisition of the sequence of focus plane images is performed by sensors in and/or on the scanner and/or by sensors on the object and/or by sensors in the room where the scanner and the object are located.

The motion sensors may be small sensor such as micro-electromechanical systems (MEMS) motion sensors. The motion sensors may measure all motion in 3D, i.e., both translations and rotations for the three principal coordinate axes. The benefits are:

Motion sensors can detect motion, also vibrations and/or shaking. Scans such affected can e.g. be corrected by use of the compensation techniques described.

Motion sensors can help with stitching and/or registering partial scans to each other. This advantage is relevant when the field of view of the scanner is smaller than the object to be scanned. In this situation, the scanner is applied for small regions of the object (one at a time) that then are combined to obtain the full scan. In the ideal case, motion sensors can provide the required relative rigid-motion transformation between partial scans' local coordinates, because they measure the relative position of the scanning device in each partial scan. Motion sensors with limited accuracy can still provide a first guess for a software-based stitching/registration of partial scans based on, e.g., the Iterative Closest Point class of algorithms, resulting in reduced computation time.

Even if it is too inaccurate to sense translational motion, a 3-axis accelerometer can provide the direction of gravity relative to the scanning device. Also a magnetometer can provide directional information relative to the scanning device, in this case from the earth's magnetic field. Therefore, such devices can help with stitching/registration.

In some embodiments the motion is determined by means of a texture image sensor having a depth of focus which is larger than the depth of focus of the focusing optics.

In some embodiments the motion is determined by determining the position and orientation of one or more of the sensors.

In some embodiments the motion is determined by means of one or more physical components arranged in the hand-held scanner.

In some embodiments the motion is determined by means of 3D position sensors.

In some embodiments the motion is determined by means of optical tracking.

The optical tracking may comprise LED(s) and camera(s), where the LED(s) may flash and the flashing can be detected by the camera(s).

In some embodiments the motion is determined by means of one or more gyroscopes.

A gyroscope is a device for measuring or maintaining orientation, based on the principles of conservation of angular momentum. A mechanical gyroscope is essentially a spinning wheel or disk whose axle is free to take any orientation. The gyroscopes used to determine the orientation of the sensor may be mechanical gyroscopes, electronic, microchip-packaged MEMS gyroscope devices, solid state ring lasers, fibre optic gyroscopes, quantum gyroscope and/or the like.

In some embodiments the motion is determined by means of one or more accelerometers.

In some embodiments the motion is determined by means of one or more magnetometers.

In some embodiments the motion is determined by means of one or more electromagnetic coils.

In some embodiments the motion is determined by means of a computerized measurement arm.

The measurement arm may for instance be from FARO Technologies. There may be goniometers in the measurement arm for measuring the movements of the arm.

In some embodiments the motion is determined by means of one or more axes on which the sensor is configured to move.

An example of an axes based system is a coordinate measuring machine (CMM), which is a device for measuring the physical geometrical characteristics of an object. This machine may be computer controlled. A typical CMM is composed of three axes, X, Y and Z, and these axes are orthogonal to each other in a typical three dimensional coordinate system. Each axis has a scale system that indicates the location of that axis. Measurements may be defined by a probe attached to the third moving axis of this machine, and the machine will read the input from the touch probe. Probes may be mechanical, optical, laser, or white light, among others.

In some embodiments the axes on which the sensor is configured to move are translational and/or rotational axes.

For each focus plane image that is acquired there is six degrees of freedom of the sensor, e.g. the handheld scanner, since the scanner is a rigid body which can perform motion in a three dimensional space, where the motion can be translation in three perpendicular axes, x, y, z, which is movement forward/backward, up/down, left/right, and this is combined with rotation about the three perpendicular axes. Thus the motion has six degrees of freedom as the movement along each of the three axes is independent of each other and independent of the rotation about any of these axes.

3D Modeling 3D modeling is the process of developing a mathematical, wireframe representation of any three-dimensional object, called a 3D model, via specialized software. Models may be created automatically, e.g. 3D models may be created using multiple approaches, such as use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

Obtaining a three dimensional representation of the surface of an object by scanning the object in a 3D scanner can be denoted 3D modeling, which is the process of developing a mathematical representation of the three-dimensional surface of the object via specialized software. The product is called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner may describe the distance to a surface at each point in the picture.

For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

3D scanners may be fixed or stationary desktop scanners into which for example a dental impression, an ear canal impression or a casted gypsum model of teeth can be placed for scanning. 3D scanners may also be handheld intraoral scanners for scanning a patient directly in the mouth or handheld or fixed ear scanners for scanning a patient directly in the ear.

Thus a 3D scanner may be a handheld scanner where scanner and object are not arranged stationary relative to each other and where the relative motion may be unlimited, a desktop scanner where the object and the scanning means, e.g. light source and camera, are arranged stationary relative to each other, a stationary scanner where the object for example can move relative to the stationary scanner etc.

A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time.

An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

Confocal scanning or focus scanning may also be used, where in-focus images are acquired at different depth to reconstruct the 3D model.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

Aligning/Registration

In some embodiments the motion between at least two subsequent 3D surfaces are determined by aligning/registering the at least two subsequent 3D surfaces.

This may be performed by means of the method of iterative closest point (ICP) or similar methods. The method of Iterative Closest Point (ICP) can be used for aligning, and it is employed to minimize the difference between two clouds of points. ICP can be used to reconstruct 2D or 3D surfaces from different scan. ICP iteratively revises the transformation, i.e. translation or rotation, needed to minimize the distance between the points of two raw scans or subscans. The input for ICP may be points from two raw scans or subscans, initial estimation of the transformation, and criteria for stopping the iteration. The output will thus be a refined transformation.

The alignment may be performed in two steps, where the first step is a subscan to subscan alignment, and the second step is a subscan to provisional virtual 3D model (combined model) alignment. The start guess for the alignment may be determined by using the gyroscopes, estimated speed of the scanner etc.

Additionally and/or alternatively, the method of least squares fit can be used in alignment.

In some embodiments aligning/registering is performed by selecting corresponding points on the at least two 3D surfaces, and minimizing the distance between the at least two 3D surfaces.

Corresponding points may the closest points on two surfaces, or point determined by a normal vector from a point on the other surface etc.

The distance may be minimized with regards to translation and rotation.

In some embodiments aligning/registration is continued in an iterative process to obtain an improved motion estimation.

In some embodiments the sensor position of each sequence is determined based on the alignment.

In some embodiments aligning comprises aligning the coordinate systems of at least two 3D surfaces.

In some embodiments aligning comprises aligning by means of matching/comparing one or more specific features, such as one or more specific features common to the at least two 3D surfaces, such as the margin line.

In some embodiments aligning comprises aligning by means of matching/comparing one or more peripheral features of the at least two 3D surfaces.

In some embodiments aligning comprises registration of the at least two 3D surfaces.

In some embodiments aligning comprises applying a predefined criterion for maximum allowed error in the registration.

In some embodiments the motion compensation comprises reconstructing a self-consistent surface model and motion and/or rotation of the scanner relative to the object from two or more scans of the object where two successive scans overlap at least partially.

Focus Scanning

The 3D scanner may be used for providing a 3D surface registration of objects using light as a non-contact probing agent. The light may be provided in the form of an illumination pattern to provide a light oscillation on the object. The variation/oscillation in the pattern may be spatial, e.g. a static checkerboard pattern, and/or it may be time varying, for example by moving a pattern across the object being scanned. The invention provides for a variation of the focus plane of the pattern over a range of focus plane positions while maintaining a fixed spatial relation of the scanner and the object. It does not mean that the scan must be provided with a fixed spatial relation of the scanner and the object, but merely that the focus plane can be varied (scanned) with a fixed spatial relation of the scanner and the object. This provides for a hand held scanner solution based on the present invention.

In some embodiments the signals from the array of sensor elements are light intensity.

One embodiment of the invention comprises a first optical system, such as an arrangement of lenses, for transmitting the probe light towards the object and a second optical system for imaging light returned from the object to the camera. In the preferred embodiment of the invention only one optical system images the pattern onto the object and images the object, or at least a part of the object, onto the camera, preferably along the same optical axis, however along opposite optical paths.

In the preferred embodiment of the invention an optical system provides an imaging of the pattern onto the object being probed and from the object being probed to the camera. Preferably, the focus plane is adjusted in such a way that the image of the pattern on the probed object is shifted along the optical axis, preferably in equal steps from one end of the scanning region to the other. The probe light incorporating the pattern provides a pattern of light and darkness on the object. Specifically, when the pattern is varied in time for a fixed focus plane then the in-focus regions on the object will display an oscillating pattern of light and darkness. The out-of-focus regions will display smaller or no contrast in the light oscillations.

Generally we consider the case where the light incident on the object is reflected diffusively and/or specularly from the object's surface. But it is understood that the scanning apparatus and method are not limited to this situation. They are also applicable to e.g. the situation where the incident light penetrates the surface and is reflected and/or scattered and/or gives rise to fluorescence and/or phosphorescence in the object. Inner surfaces in a sufficiently translucent object may also be illuminated by the illumination pattern and be imaged onto the camera. In this case a volumetric scanning is possible. Some planktic organisms are examples of such objects.

When a time varying pattern is applied a single sub-scan can be obtained by collecting a number of 2D images at different positions of the focus plane and at different instances of the pattern. As the focus plane coincides with the scan surface at a single pixel position, the pattern will be projected onto the surface point in-focus and with high contrast, thereby giving rise to a large variation, or amplitude, of the pixel value over time. For each pixel it is thus possible to identify individual settings of the focusing plane for which each pixel will be in focus. By using knowledge of the optical system used, it is possible to transform the contrast information vs. position of the focus plane into 3D surface information, on an individual pixel basis.

Thus, in one embodiment of the invention the focus position is calculated by determining the light oscillation amplitude for each of a plurality of sensor elements for a range of focus planes.

For a static pattern a single sub-scan can be obtained by collecting a number of 2D images at different positions of the focus plane. As the focus plane coincides with the scan surface, the pattern will be projected onto the surface point in-focus and with high contrast. The high contrast gives rise to a large spatial variation of the static pattern on the surface of the object, thereby providing a large variation, or amplitude, of the pixel values over a group of adjacent pixels. For each group of pixels it is thus possible to identify individual settings of the focusing plane for which each group of pixels will be in focus. By using knowledge of the optical system used, it is possible to transform the contrast information vs. position of the focus plane into 3D surface information, on an individual pixel group basis.

Thus, in one embodiment of the invention the focus position is calculated by determining the light oscillation amplitude for each of a plurality of groups of the sensor elements for a range of focus planes.

The 2D to 3D conversion of the image data can be performed in a number of ways known in the art. I.e. the 3D surface structure of the probed object can be determined by finding the plane corresponding to the maximum light oscillation amplitude for each sensor element, or for each group of sensor elements, in the camera's sensor array when recording the light amplitude for a range of different focus planes. Preferably, the focus plane is adjusted in equal steps from one end of the scanning region to the other. Preferably the focus plane can be moved in a range large enough to at least coincide with the surface of the object being scanned.

The scanner preferably comprises at least one beam splitter located in the optical path. For example, an image of the object may be formed in the camera by means of a beam splitter. Exemplary uses of beam splitters are illustrated in the figures.

In a preferred embodiment of the invention light is transmitted in an optical system comprising a lens system. This lens system may transmit the pattern towards the object and images light reflected from the object to the camera.

In a telecentric optical system, out-of-focus points have the same magnification as in-focus points. Telecentric projection can therefore significantly ease the data mapping of acquired 2D images to 3D images. Thus, in a preferred embodiment of the invention the optical system is substantially telecentric in the space of the probed object. The optical system may also be telecentric in the space of the pattern and camera.

The present invention relates to different aspects including the method described above and in the following, and corresponding methods, devices, apparatuses, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for detecting a movable object in a location, when scanning a rigid object in the location by means of a 3D scanner for generating a virtual 3D model of the rigid object, wherein the system comprises:

means for providing a first 3D representation of at least part of a surface by scanning at least part of the location;

means for providing a second 3D representation of at least part of the surface by scanning at least part of the location;

means for determining for the first 3D representation a first excluded volume in space where no surface can be present;

means for determining for the second 3D representation a second excluded volume in space where no surface can be present;

means for disregarding the portion of the surface in the first 3D representation in the generation of the virtual 3D model, if a portion of the surface in the first 3D representation is located in space in the second excluded volume, and/or means for disregarding the portion of the surface in the second 3D representation in the generation of the virtual 3D model, if a portion of the surface in the second 3D representation is located in space in the first excluded volume.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 13a through 13e show an example of acquiring a first and a second representation of a surface of an object, where no movable object is present.

FIGS. 14a through 14e shows an example of acquiring a first and a second representation of a surface of an object, where a movable object of the second representation is present in the excluded volume of the first representation.

FIGS. 15a through 15e show an example of acquiring a first and a second representation of a surface of an object, where a possible movable object is present in the second representation, but not in the excluded volume of the first representation.

FIGS. 20*a* through 20*d* show examples of the principle of a far threshold distance from the captured surface defining a volume which is not included in the excluded volume of a representation.

DETAILED DESCRIPTION

In the following description, reference is made to the accompanying figures, which show by way of illustration how the invention may be practiced.

Figure 1:
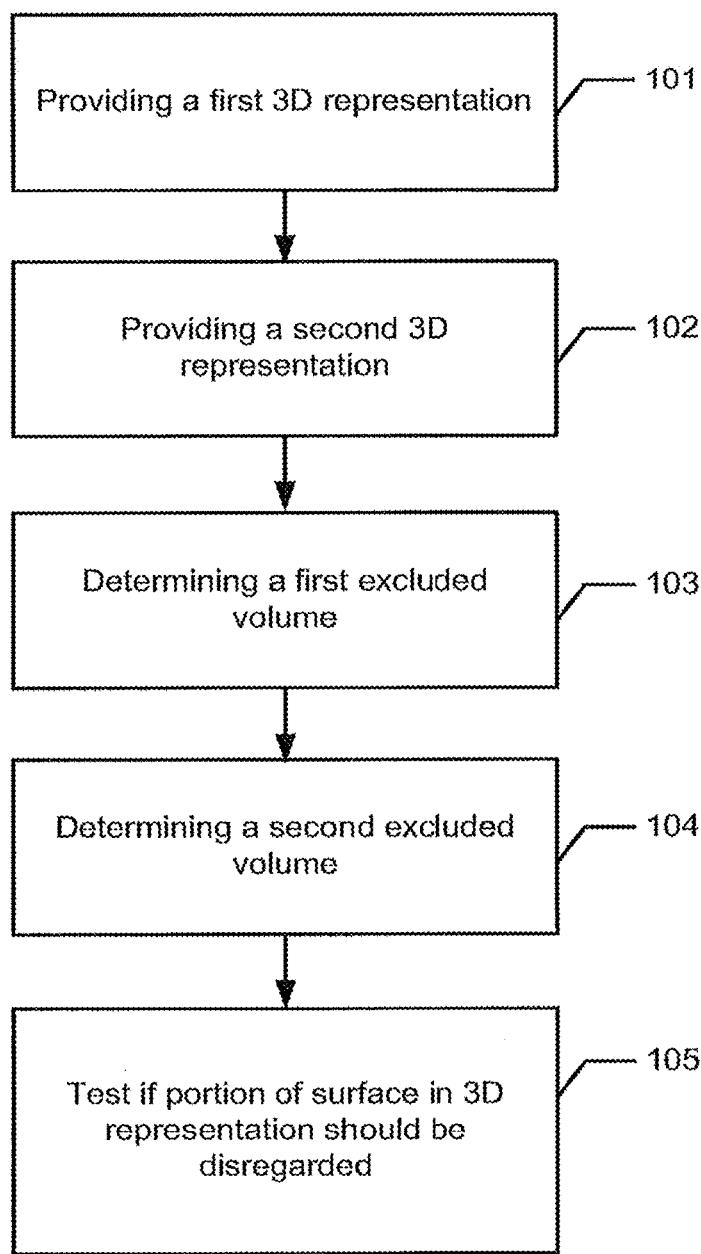
FIG. 1 shows an example of a flowchart of the method for detecting a movable object in a location, when scanning a rigid object in the location by means of a 3D scanner for generating a virtual 3D model of the rigid object.

FIG. 1 shows an example of a flowchart of the method for detecting a movable object in a location, when scanning a rigid object in the location by means of a 3D scanner for generating a virtual 3D model of the rigid object. In step 101 a first 3D representation of at least part of a surface is provided by scanning at least part of the location.

In step 102 a second 3D representation of at least part of the surface is provided by scanning at least part of the location.

In step 103 a first excluded volume in space where no surface can be present is determined for the first 3D representation.

In step 104 a second excluded volume in space where no surface can be present is determined for the second 3D representation.

In step 105 a portion of the surface in the first 3D representation is disregarded in the generation of the virtual 3D model, if the portion of the surface in the first 3D representation is located in space in the second excluded volume, and/or a portion of the surface in the second 3D representation is disregarded in the generation of the virtual 3D model, if the portion of the surface in the second 3D representation is located in space in the first excluded volume.

Figure 2:
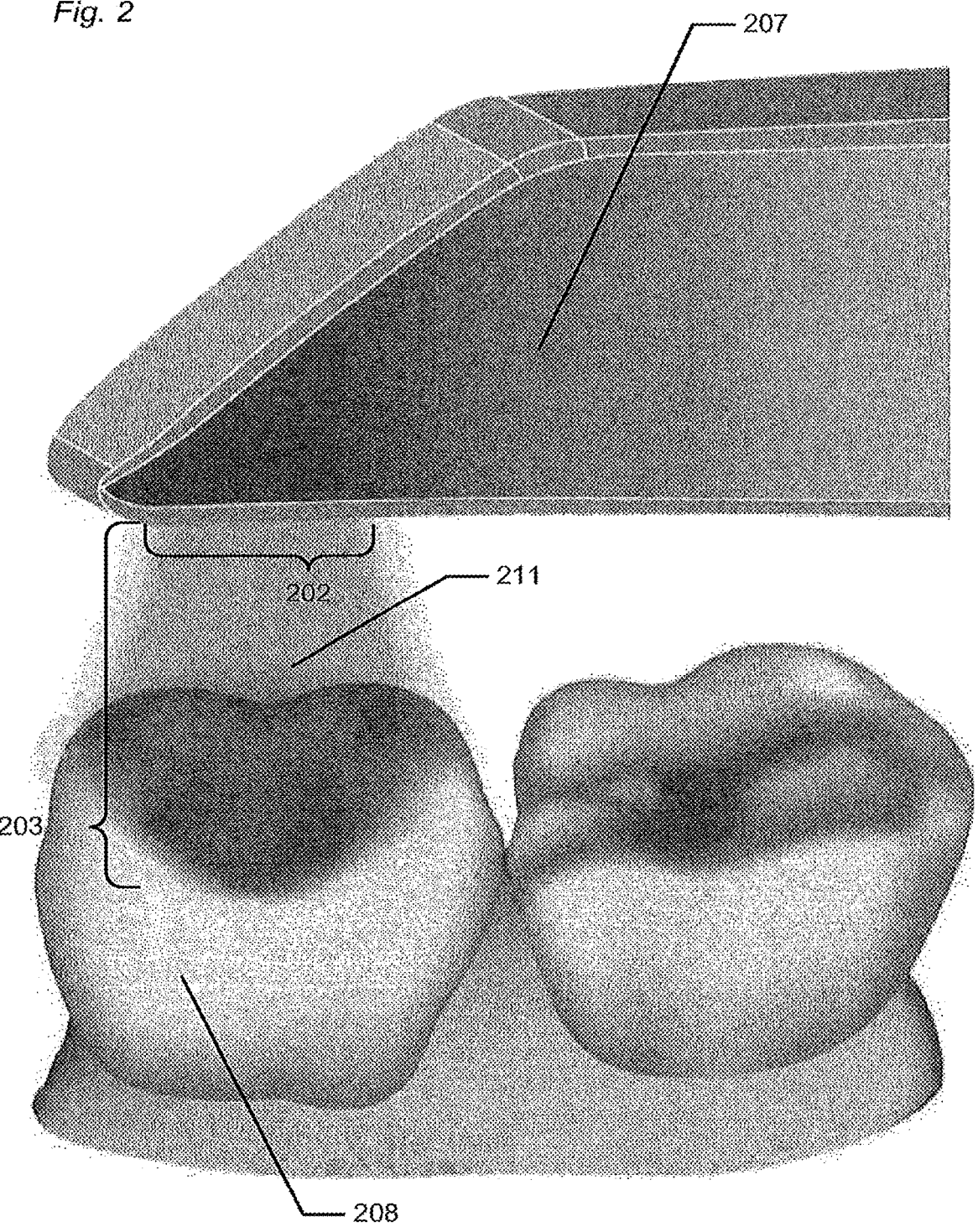
FIG. 2 shows an example of a scan head of an intraoral 3D scanner scanning a set of teeth.

FIG. 2 shows an example of a scan head of an intraoral 3D scanner scanning a set of teeth. An intraoral handheld 3D scanner (not shown) comprising a scan head 207 is scanning a tooth 208. The scanning is performed by transmitting light rays on the tooth 208. The light rays forms a scan volume 211, which is cone shaped in this example.

The length 203 of the scan volume 211, i.e. the distance from the opening 202 of the scan head to the end of the scan volume may be for example about 5 mm, 10 mm, 15 mm, 16 mm, 17 mm, 18 mm, 19 mm, 20 mm, 25 mm, 30 mm.

The scan volume may be about 20 mm×20 mm.

Figure 3:
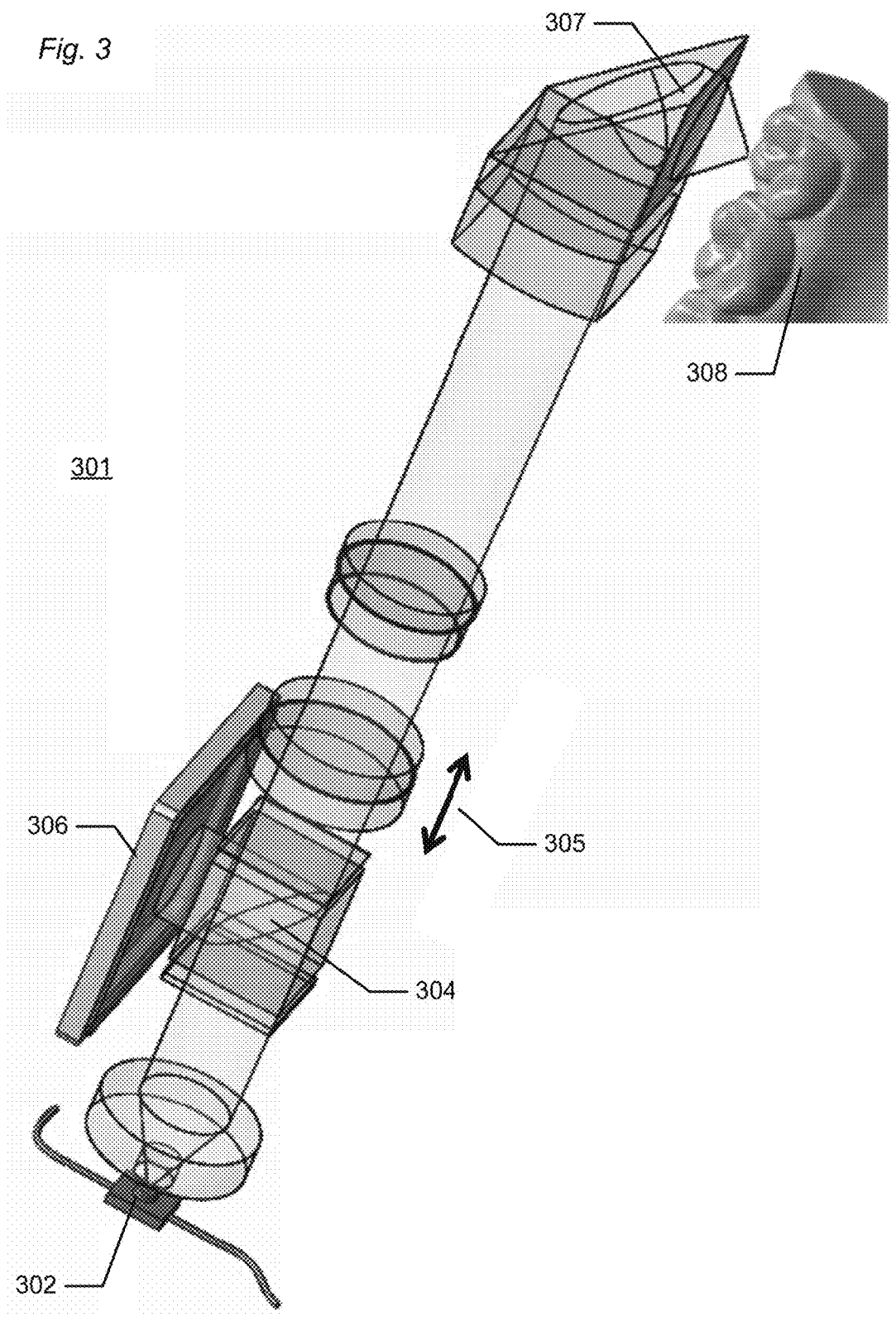
FIG. 3 shows an example of a handheld 3D scanner.

FIG. 3 shows an example of a handheld 3D scanner.

The handheld scanner 301 comprises a light source 302 for emitting light, a beam splitter 304, movable focus optic 305, such as lenses, an image sensor 306, and a tip or probe 307 for scanning an object 308. In this example the object 308 is teeth in an intra oral cavity.

The scanner comprises a scan head or tip or probe 307 which can be entered into a cavity for scanning an object 308. The light from the light source 302 travels back and forth through the optical system. During this passage the optical system images the object 308 being scanned onto the image sensor 306. The movable focus optics comprises a focusing element which can be adjusted to shift the focal imaging plane on the probed object 308. One way to embody the focusing element is to physically move a single lens element back and forth along the optical axis. The device may include polarization optics and/or folding optics which directs the light out of the device in a direction different to the optical axis of the lens system, e.g. in a direction perpendicular to the optical axis of the lens system. As a whole, the optical system provides an imaging onto the object being probed and from the object being probed to the image sensor, e.g. camera. One application of the device could be for determining the 3D structure of teeth in the oral cavity. Another application could be for determining the 3D shape of the ear canal and the external part of the ear.

The optical axis in FIG. 3 is the axis defined by a straight line through the light source, optics and the lenses in the optical system. This also corresponds to the longitudinal axis of the scanner illustrated in FIG. 3. The optical path is the path of the light from the light source to the object and back to the camera. The optical path may change direction, e.g. by means of beam splitter and folding optic.

The focus element is adjusted in such a way that the image on the scanned object is shifted along the optical axis, for example in equal steps from one end of the scanning region to the other. A pattern may be imaged on the object, and when the pattern is varied in time in a periodic fashion for a fixed focus position then the in-focus regions on the object will display a spatially varying pattern. The out-of-focus regions will display smaller or no contrast in the light variation. The 3D surface structure of the probed object may be determined by finding the plane corresponding to an extremum in the correlation measure for each sensor in the image sensor array or each group of sensor in the image sensor array when recording the correlation measure for a range of different focus positions. Preferably one would move the focus position in equal steps from one end of the scanning region to the other. The distance from one end of the scanning region to the other may be such as 5 mm, 10 mm, 15 mm, 16 mm, 20 mm, 25 mm, 30 mm etc.

Figures 4A, 4B:
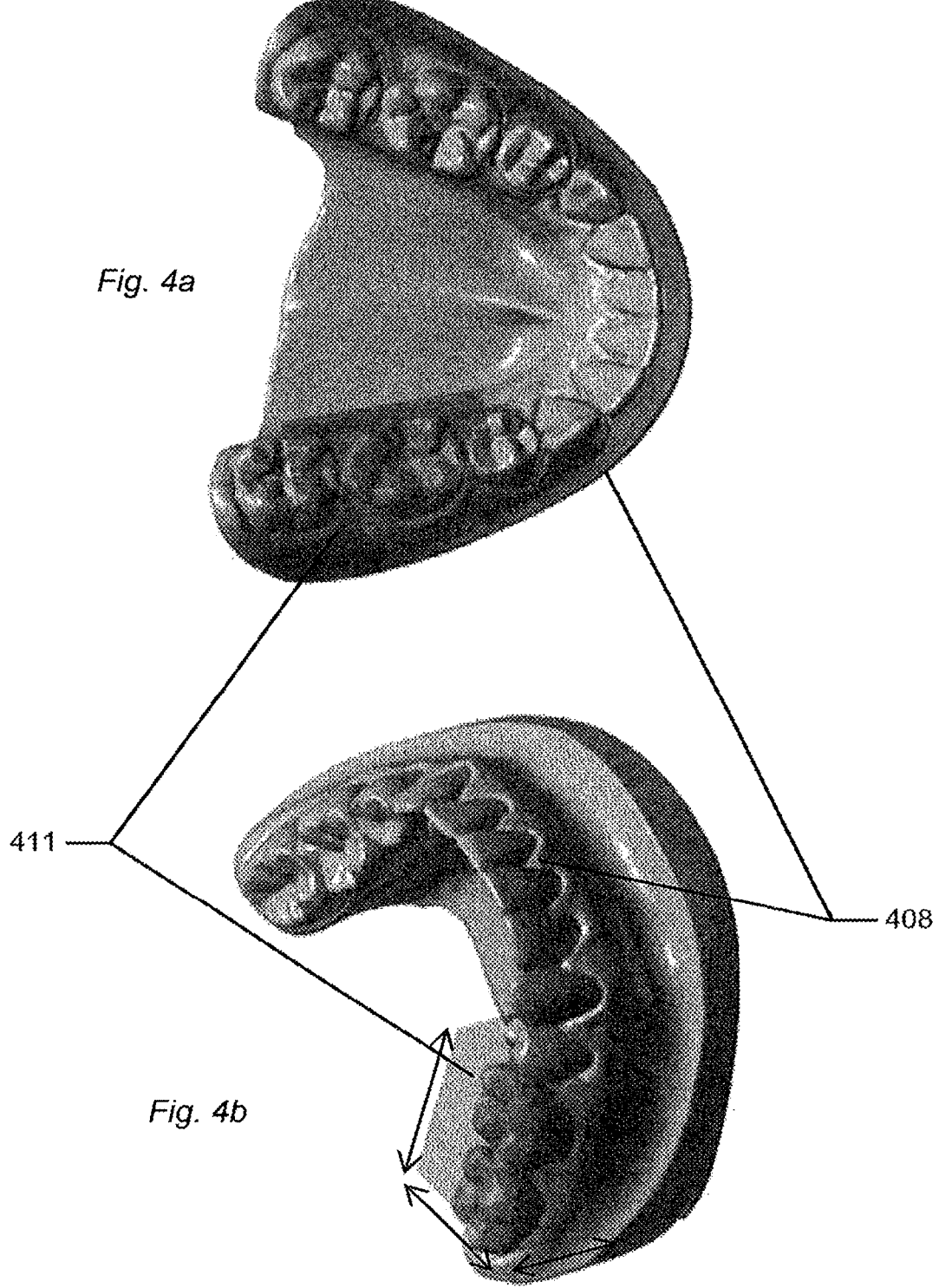
FIGS. 4a and 4b shows an example of a section of teeth in the mouth which can be covered in a sub-scan.

FIG. 4 shows an example of a section of teeth in the mouth which can be covered in a sub-scan. In FIG. 4*a* the teeth 408 are seen in a top view, and in FIG. 4*b* the teeth 408 are seen in a perspective view.

An example of the scan volume 411 for one sequence of focus plane images is indicated by the transparent box. The scan volume may be such as 17×15×20 mm, where the 15 mm may be the "height" of the scan volume corresponding to the distance the focus optics can move.

Figure 5:
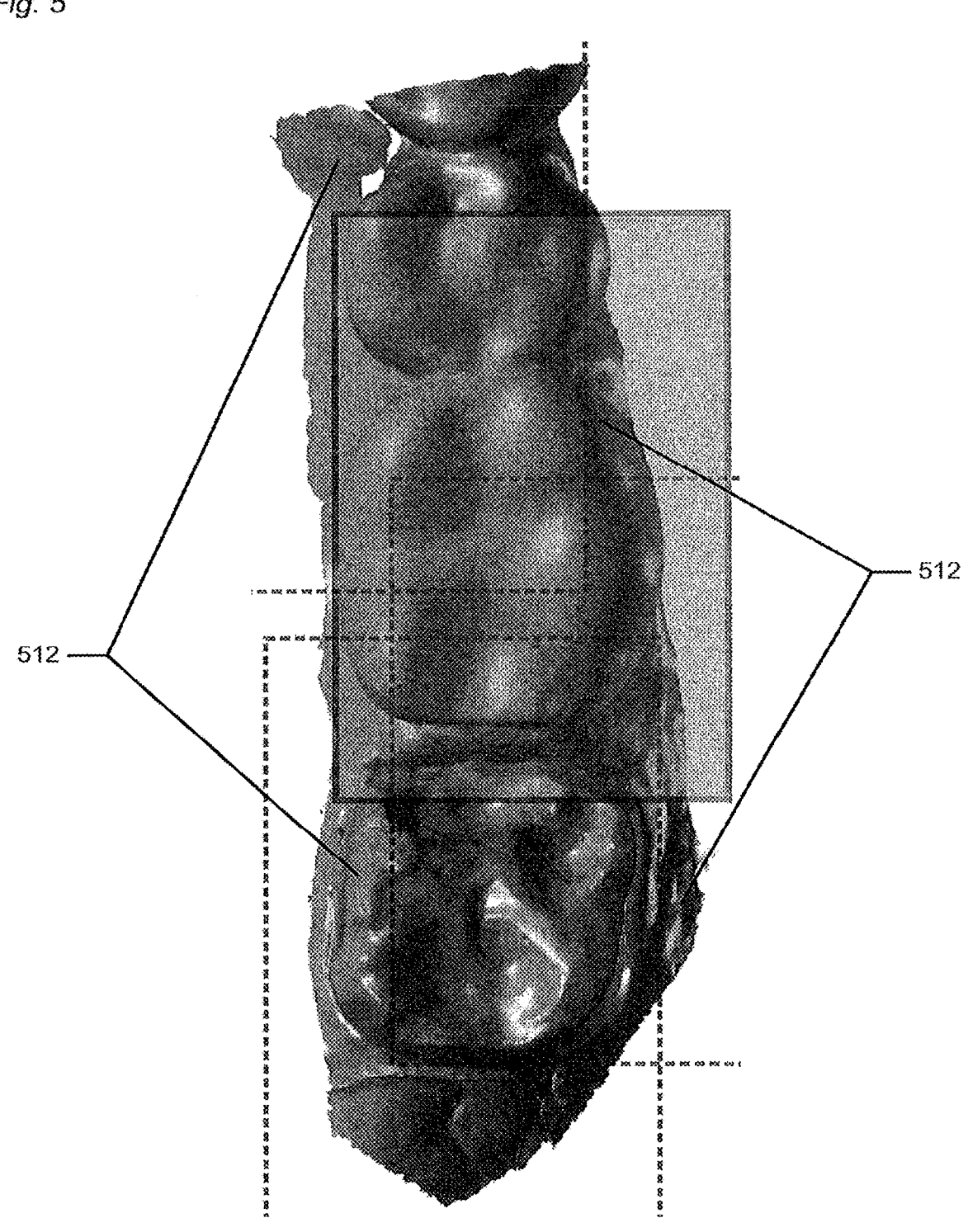
FIG. 5 shows an example of how the different sub-scans generating 3D surfaces are distributed across a set of teeth.

FIG. 5 shows an example of how the different sub-scans generating 3D surfaces is distributed across a set of teeth.

Four sub-scans 512 are indicated on the figure. Each sub-scan provides a 3D surface of the scanned teeth. The 3D surfaces may be partly overlapping, whereby a motion of the scanner performed during the acquisition of the sub-scans can be determined by comparing the overlapping parts of two or more 3D surfaces.

FIG. 6 shows an example of registering/aligning representations of 3D surfaces and compensating for motion in a 3D surface.

Figures 6A, 6B, 6C, 6D, 6E:
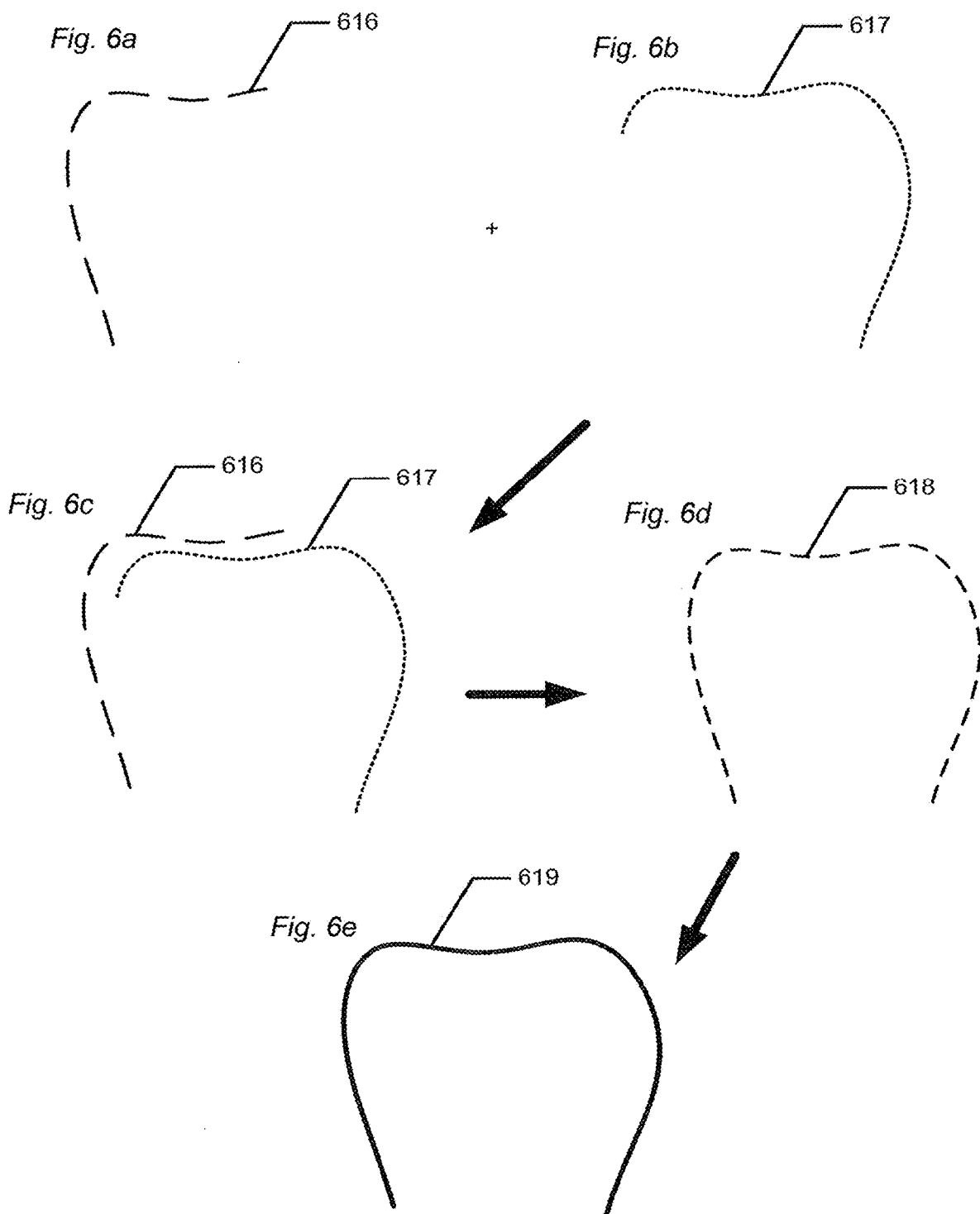
FIGS. 6a through 6e shows an example of registering/aligning representations of 3D surfaces and compensating for motion in a 3D surface.

FIG. 6*a* shows a 3D surface 616, which for example may be generated from a number of focus plane images.

FIG. 6*b* shows another 3D surface 617, which may have been generated in a subsequent sequence of focus plane images.

FIG. 6*c* shows the two 3D surface 616, 617 are attempted to be aligned/registered. Since the two 3D surfaces 616, 617 have 3D points which correspond to the same area of a tooth, it is possible to perform the registration/alignment by ICP, by comparing the corresponding points in the two 3D surfaces etc.

FIG. 6*d* shows the resulting 3D surface 618 when the two 3D surfaces 616, 617 have been merged together.

FIG. 6*e* shows that based on the resulting 3D surface 618 the relative motion performed by the scanner during the acquisition of the sub-scans or focus plane images generating 3D surface 616 and 617 can be determined, and based on this determined motion the resulting 3D surface 618 can be corrected to a final "correct" 3D surface 619.

Figure 7:
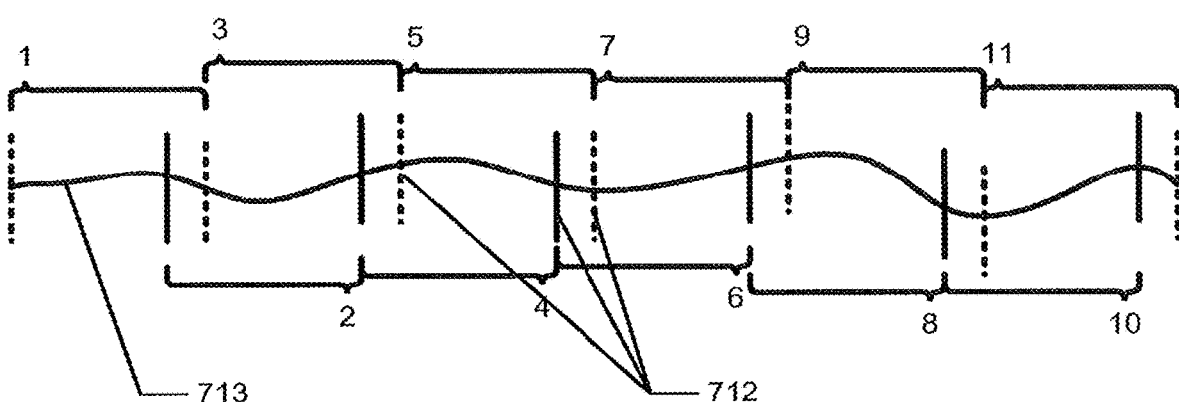
FIG. 7 shows an example of a 3D surface where overlapping sub-scans are indicated.

FIG. 7 shows an example of a 3D surface where overlapping sub-scans are indicated.

A number of 3D representations or sub-scans are indicated by the numbers 1-11 and the subdivision markers 712 on a 3D surface 713. The subdivision markers 712 for sub-scans 1, 3, 5, 7, 9, and 11 are with dotted lines, and the subdivision markers for sub-scan 2, 4, 6, 8, 10 are marked with full lines. The sub-scans are all overlapping with the same distance, but the overlapping distance may be different for each pair of subscans. As typically a dentist will hold the scanner and move it across the teeth of the patient, the overlapping distance depends on how fast the dentist moves the scanner and the time frame between the acquisition of each scan, so if the time frame is constant, and the dentist does not move the scanner exactly with a constant speed, the overlapping distance will not be the same for all subscans.

Figure 8:
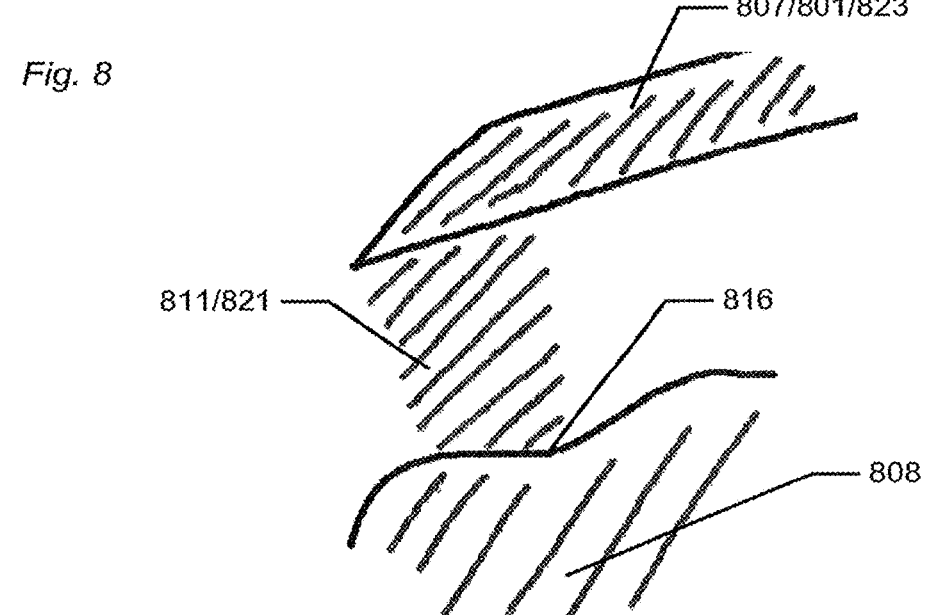
FIG. 8 shows an example of excluded volume.

FIG. 8 shows an example of excluded volume.

The excluded volume 821 is the volume in space where no surface can be present. At least a part of the excluded volume 821 may correspond to the scan volume 811 of a 3D representation, since the space between the scan head 807 or the focusing optics of the 3D scanner and the captured surface 816 must be an empty space, unless a transparent object, which is not detectable by the 3D scanner, was located in the scan volume. Furthermore the volume of the scan head 807 and the 3D scanner 801 may be defined as an excluded volume 823, since the scanner and scan head occupies their own volume in space, whereby no surface can be present there. Furthermore, the tooth 808 which is being scanned also occupies a volume in space, but since the surface 816 of the tooth 808 is being captured by the scanner, it is not considered what is "behind" the surface 816.

FIG. 9 shows an example of scanning a tooth and acquiring a first and a second representation of the surface of the tooth, where no movable object is present.

Figures 9A, 9B:
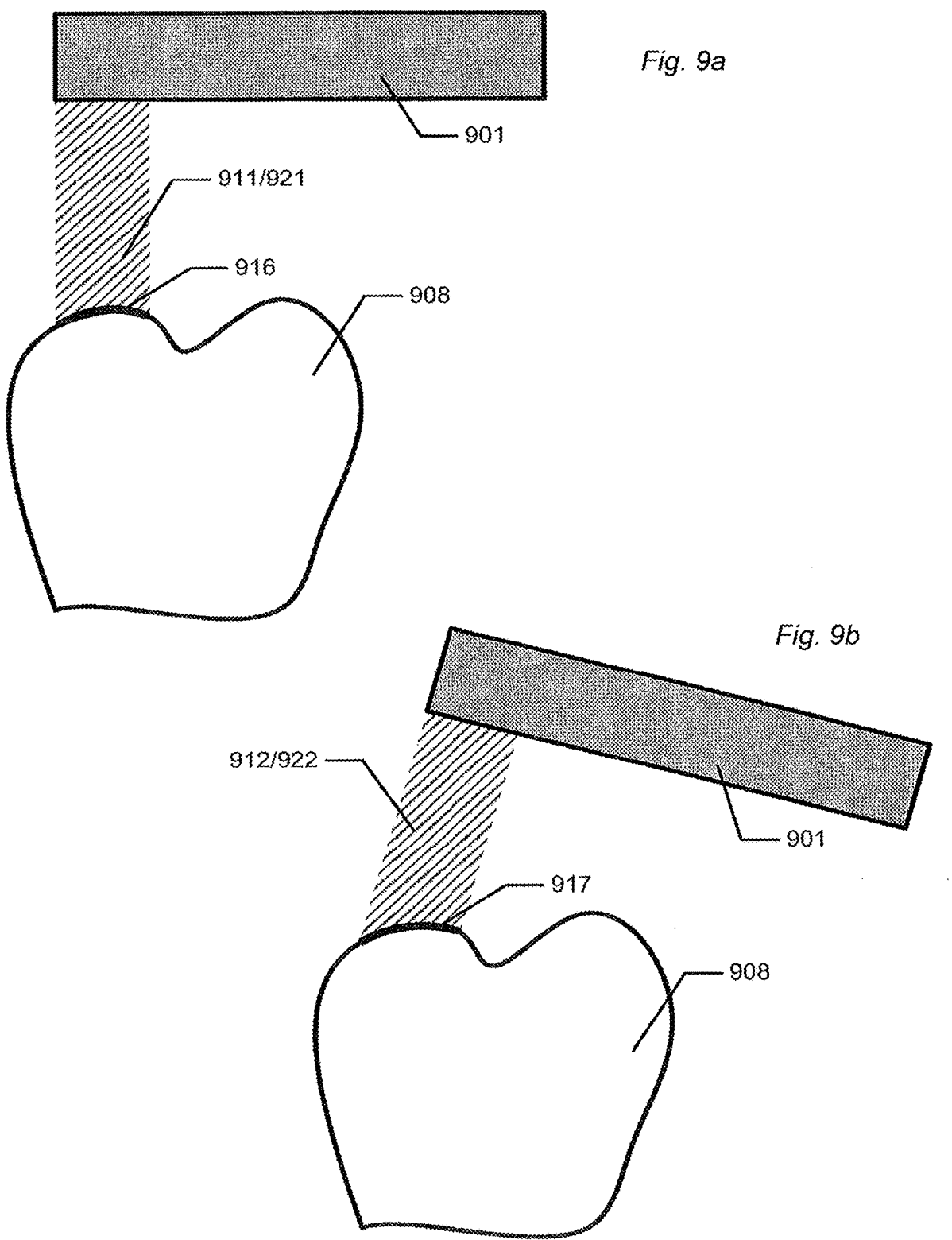
FIGS. 9a and 9b show an example of scanning a tooth and acquiring a first and a second representation of the surface of the tooth, where no movable object is present.

FIG. 9*a* shows an example of scanning the tooth 908 using a 3D scanner 901 for acquiring a first 3D representation 916 of the surface of the tooth 908. A first scan volume 911 in space is related to the first representation, and a first excluded volume 921 corresponds to the first scan volume 911.

FIG. 9*b* shows an example of scanning the tooth 908 using a 3D scanner 901 for acquiring a second 3D representation 917 of the surface of the tooth 908. A second scan volume 912 in space is related to the second representation, and a second excluded volume 922 corresponds to the second scan volume 912. The second representation is acquired with a different angle between scanner and tooth than the first representation.

No surface portion of the first representation 916 lies in the second excluded volume 922, and no surface portion of the second representation 917 lies in the first excluded volume 921, so no surface portion(s) are disregarded in the generation of the virtual 3D model in this case.

FIG. 10 shows an example of scanning a tooth and acquiring a first and a second representation of the surface of the tooth, where a movable object is captured in part of the first representation.

Figures 10A, 10B:
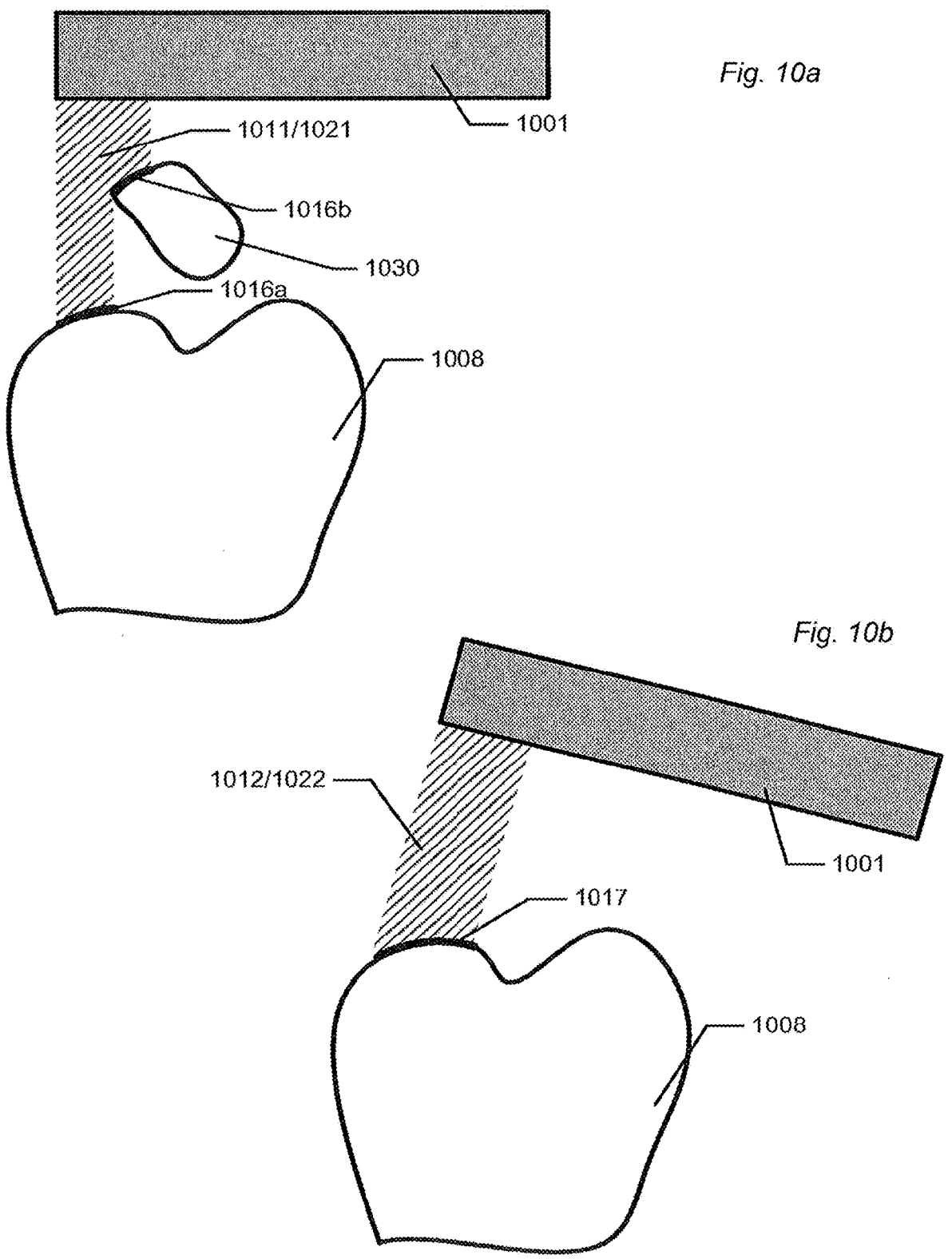
FIGS. 10a and 10b show an example of scanning a tooth and acquiring a first and a second representation of the surface of the tooth, where a movable object is captured in part of the first representation.

FIG. 10*a* shows an example of scanning the tooth 1008 using a 3D scanner 1001 for acquiring a first 3D representation 1016 of the surface of the tooth 1008. A movable object 1030 is present, and a part 1016*b* of the first representation 1016 comprises the surface of the movable object 1030. The part 1016*a* of the first representation 1016 comprises the surface of the tooth. A first scan volume 1011 in space is related to the first representation, and a first excluded volume 1021 corresponds to the first scan volume 1011.

FIG. 10*b* shows an example of scanning the tooth 1008 using a 3D scanner 1001 for acquiring a second 3D representation 1017 of the surface of the tooth 1008. A second scan volume 1012 in space is related to the second representation, and a second excluded volume 1022 corresponds to the second scan volume 1012. The second representation is acquired with a different angle between scanner and tooth than the first representation.

Since the surface portion 1016*b* of the first representation 1016 lies in the second excluded volume 1022, this surface portion 1016*b* is disregarded in the generation of the virtual 3D model.

FIG. 11 shows an example of scanning a tooth and acquiring a first and a second representation of the surface of the tooth, where a movable object is captured in the second representation.

Figures 11A, 11B:
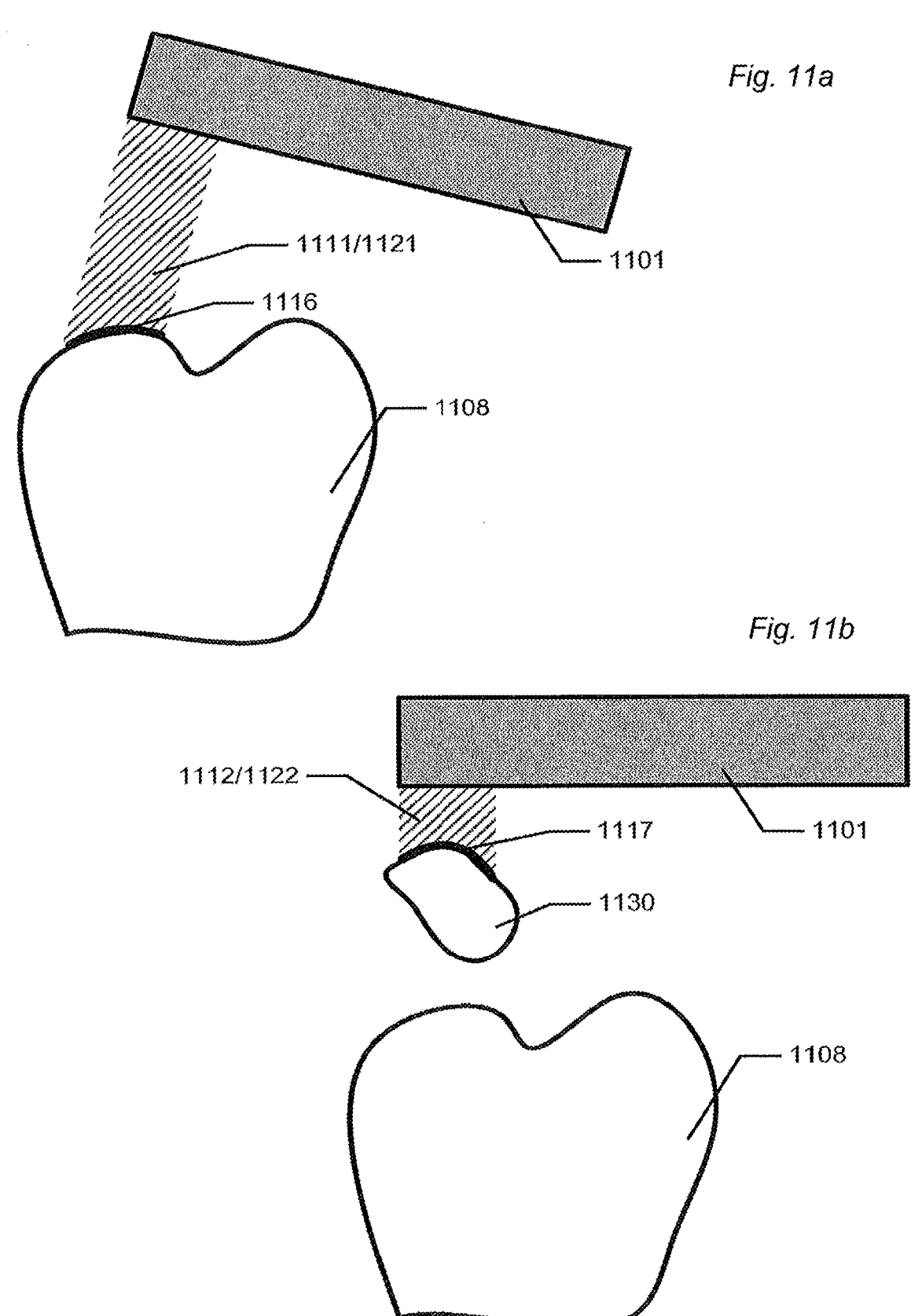
FIGS. 11a and 11b show an example of scanning a tooth and acquiring a first and a second representation of the surface of the tooth, where a movable object is captured in the second representation.

FIG. 11*a* shows an example of scanning the tooth 1108 using a 3D scanner 1101 for acquiring a first 3D representation 1116 of the surface of the tooth 1108. A first scan volume 1111 in space is related to the first representation, and a first excluded volume 1121 corresponds to the first scan volume 1111.

FIG. 11*b* shows an example of scanning the tooth 1108 using a 3D scanner 1101 for acquiring a second 3D representation 1117 of the surface of the tooth 1108. A movable object 1130 is present, and the second representation 1117 comprises the surface of the movable object 1130. A second scan volume 1112 in space is related to the second representation, and a second excluded volume 1122 corresponds to the second scan volume 1112. The second representation is acquired with a different angle between scanner and tooth than the first representation.

Since the surface of the second representation 1117 lies in the first excluded volume 1121, the surface of the second representation 1117 is disregarded in the generation of the virtual 3D model.

The figures in FIG. 11 are shown in 2D, but it is understood that the figures represent 3D figures.

FIG. 12 shows an example of acquiring a first and a second representation of the surface of an object, e.g. a tooth, where a movable object is captured in the first representation.

Figures 12A, 12B, 12C:
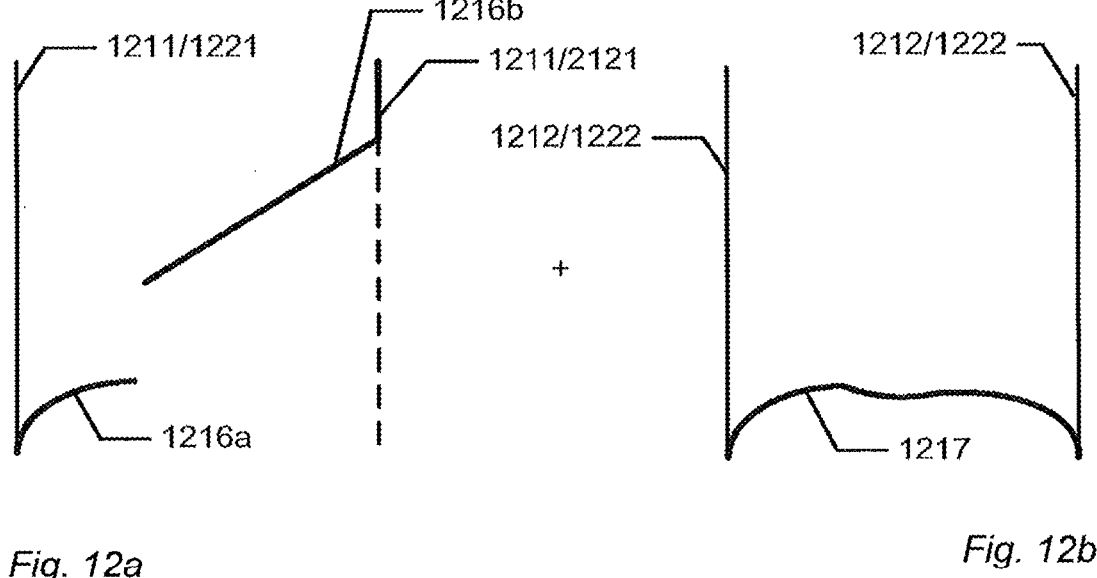
FIGS. 12a through 12c shows an example of acquiring a first and a second representation of the surface of an object, e.g. a tooth, where a movable object is captured in the first representation.

FIG. 12*a* shows a first 3D representation 1216 comprising two parts, part 1216*a* and part 1216*b*. The first scan volume 1211 is indicated by the vertical lines. The first excluded volume 1221 corresponds to the first scan volume.

FIG. 12*b* shows a second 3D representation 1217. The second scan volume 1212 is indicated by the vertical lines. The second excluded volume 1222 corresponds to the second scan volume.

The part 1216*a* of the first representation 1216 corresponds to the first part of the second representation 1217, whereas the part 1216*b* of the second representation 1216 does not correspond to the second part of the second representation 1217.

The part 1216*b* of the first representation 1216 lies in the second excluded volume 1222, and the part 1216*b* is therefore disregarded in the generation of the virtual 3D model.

FIG. 12*c* shows the resulting 3D representation 1219, which corresponds to the second representation.

The figures in FIG. 12 are shown in 2D, but it is understood that the figures represent 3D figures.

FIG. 13 shows an example of acquiring a first and a second representation of a surface of an object, where no movable object is present.

FIG. 13*a* shows an example of acquiring a first 3D representation 1316 of a surface of an object (not shown). A first scan volume 1311 in space is related to the first representation. The first scan volume 1311 is indicated by dotted vertical lines. A first excluded volume 1321 corresponds to the first scan volume 1311.

FIG. 13*b* shows an example of acquiring a second 3D representation 1317 of a surface of an object (not shown). A second scan volume 1312 in space is related to the second representation. The second scan volume 1312 is indicated by dotted vertical lines. A second excluded volume 1322 corresponds to the second scan volume 1312.

The second representation is acquired with a different angle between scanner and tooth than the first representation. Furthermore, the second representation is displaced in space relative to the first representation, so the first and second representation does not represent the same entire surface part of the object, but parts of the representations are overlapping.

FIG. 13*c* shows an example where the first representation 1316 and the second representation 1317 are aligned/registered, such that the corresponding parts of the representations are arranged in the same location.

FIG. 13*d* shows an example where the overlapping common scan volume 1340 of the first representation 1316 and the second representation 1317 is indicated as a shaded area. If a surface portion of one of the representations is located in the overlapping common scan volume 1340, then this corresponds to that the surface portion is located in the excluded volume of the other representation. However, in this case, no surface portion of the first representation 1316 or of the second representation 1317 lies in the overlapping common scan volume 1340, so no surface portion(s) are disregarded in the generation of the virtual 3D model in this case.

In order to be able to distinguish between the surface of the first and the surface of the second representation, these two surfaces are slightly displaced, but in a real case the surface of the first and the surface of the second representation may be exactly overlapping each other, so that the surface part from the first representation and the surface part from the second representation cannot be distinguished.

FIG. 13*e* shows an example of the resulting virtual 3D surface 1319.

The figures in FIG. 13 are shown in 2D, but it is understood that the figures represent 3D figures.

FIG. 14 shows an example of acquiring a first and a second representation of a surface of an object, where a movable object of the second representation is present in the excluded volume of the first representation.

FIG. 14*a* shows an example of acquiring a first 3D representation 1416 of a surface of an object (not shown). A first scan volume 1411 in space is related to the first representation. The first scan volume 1411 is indicated by dotted vertical lines. A first excluded volume 1421 corresponds to the first scan volume 1411.

FIG. 14*b* shows an example of acquiring a second 3D representation 1417 of a surface of an object (not shown). A second scan volume 1412 in space is related to the second representation. The second scan volume 1412 is indicated by dotted vertical lines. A second excluded volume 1422 corresponds to the second scan volume 1412. The second 3D representation 1417 comprises two parts 1417*a* and 1417*b*. The part 1417*b* is located between the part 1417*a* and the scanner (not shown), which is arranged somewhere at the end of the scan volume.

The second representation is acquired with a different angle between scanner and tooth than the first representation. Furthermore, the second representation is displaced in space relative to the first representation, so the first and second representation does not represent the same entire surface part of the object, but parts of the representations are overlapping.

FIG. 14*c* shows an example where the first representation 1416 and the second representation 1417 are aligned/registered, such that the corresponding parts of the representations are arranged in the same location. Some of the part 1417*a* of the second representation is aligned/registered with the first representation. The part 1417*b* cannot be aligned/registered with the first representation 1416, since there is no corresponding surface portions between the surface 1416 and the surface 1417*b*.

FIG. 14*d* shows an example where the overlapping common scan volume 1440 of the first representation 1416 and the second representation 1417 is indicated as a shaded area. The surface portion 1417*b* of the second representation is located in the overlapping common scan volume 1440, and the surface portion 1417*b* of the second representation 1417 is therefore located in the excluded volume 1421 of the first representation 1416, and part 1417*b* must therefore be a movable object, which is only present in the second representation.

In order to be able to distinguish between the surface of the first and the surface of the second representation, these two surfaces are slightly displaced, but in a real case the surface of the first and the surface of the second representation may be exactly overlapping each other, so that the surface part from the first representation and the surface part from the second representation cannot be distinguished.

FIG. 14*e* shows an example of the resulting virtual 3D surface 1419, where the surface portion 1417*b* is disregarded in the generation of the virtual 3D model, so the virtual 3D model comprises the first representation 1416 and the part 1417*a* of the second representation 1417.

The figures in FIG. 14 are shown in 2D, but it is understood that the figures represent 3D figures.

FIG. 15 shows an example of acquiring a first and a second representation of a surface of an object, where a possible movable object is present in the second representation, but not in the excluded volume of the first representation.

FIG. 15*a* shows an example of acquiring a first 3D representation 1516 of a surface of an object (not shown). A first scan volume 1511 in space is related to the first representation. The first scan volume 1511 is indicated by dotted vertical lines. A first excluded volume 1521 corresponds to the first scan volume 1511.

FIG. 15*b* shows an example of acquiring a second 3D representation 1517 of a surface of an object (not shown). A second scan volume 1512 in space is related to the second representation. The second scan volume 1512 is indicated by dotted vertical lines. A second excluded volume 1522 corresponds to the second scan volume 1512. The second 3D representation 1517 comprises two parts 1517*a* and 1517*b*. The part 1517*b* is located between the part 1517*a* and the scanner (not shown), which is arranged somewhere at the end of the scan volume.

The second representation 1517 is acquired with a different angle between scanner and tooth than the first representation 1516. Furthermore, the second representation is displaced in space relative to the first representation, so the first and second representation does not represent the same entire surface part of the object, but parts of the representations are overlapping.

FIG. 15c shows an example where the first representation 1516 and the second representation 1517 are aligned/registered, such that the corresponding parts of the representations are arranged in the same location. Some of the part 1517a of the second representation is aligned/registered with the first representation 1516. The part 1517b cannot be aligned/registered with the first representation 1516, since there is no corresponding surface portions between the surface 1516 and the surface 1517b.

FIG. 15d shows an example where the overlapping common scan volume 1540 of the first representation 1516 and the second representation 1517 is indicated as a shaded area. The surface portion 1517b of the second representation is not located in the overlapping common scan volume 1540, and the surface portion 1517b of the second representation 1517 is therefore not located in the excluded volume 1521 of the first representation 1516.

In order to be able to distinguish between the surface of the first and the surface of the second representation, these two surfaces are slightly displaced, but in a real case the surface of the first and the surface of the second representation may be exactly overlapping each other, so that the surface part from the first representation and the surface part from the second representation cannot be distinguished.

FIG. 15e shows an example of the resulting virtual 3D surface 1519, where the surface portion 1517b is not disregarded in the generation of the virtual 3D model, so the virtual 3D model comprises the first representation 1516 and both parts, 1517a and 1517b, of the second representation 1517.

Even though the surface portion 1517b probably is the representation of a movable object, at least this would be assumed if the object in this case is a tooth, since a tooth is unlikely to have a protrusion like the part 1517b of the representation shows, the surface portion 1517b cannot be disregarded yet, because the surface portion 1517b is not found to be located in any excluded volume from any representation yet. But when the scanning of the object's surface continues, there will probably be acquired a third representation which has an overlapping common scan volume with the second representation, and if the surface portion 1517b is located in the excluded volume of the third representation, then the surface portion 1517b can be disregarded from the virtual 3D model.

The figures in FIG. 15 are shown in 2D, but it is understood that the figures represent 3D figures.

Figure 16:
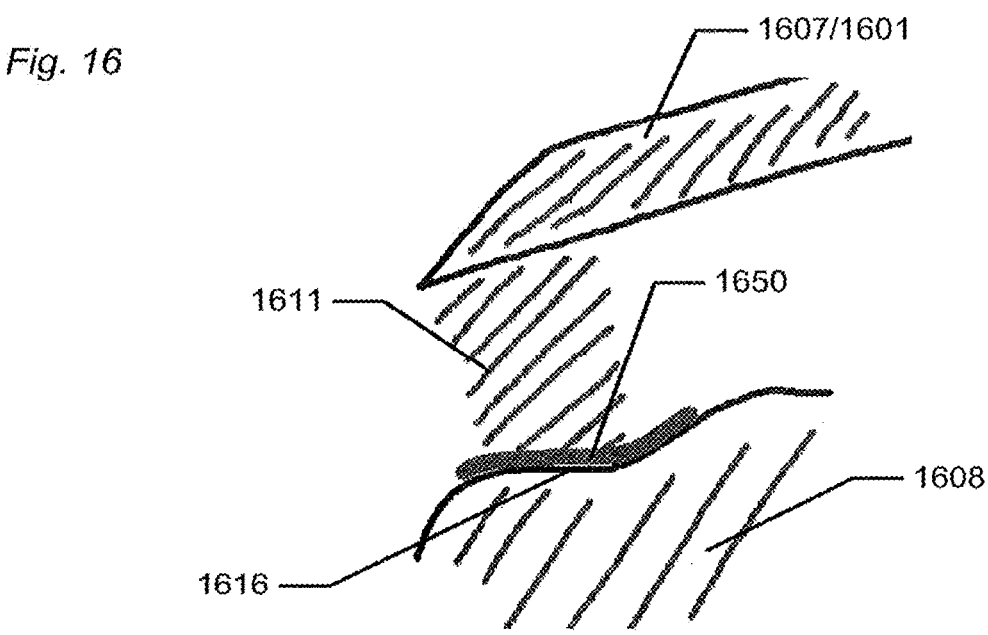
FIG. 16 shows an example of a near threshold distance defining how far from the representation possible movable objects are disregarded in the generation of the virtual 3D model.

FIG. 16 shows an example of a threshold distance defining how far from the representation or captured surface possible movable objects are disregarded in the generation of the virtual 3D model.

A near threshold distance 1650 is defined, which determines a distance from the captured surface 1616 in a first representation, where a surface portion in the second representation (not shown) which is located within the near threshold distance 1650 from the captured surface 1616 and which is located in space in the first excluded volume 1611 is not disregarded in the generation of the virtual 3D model.

The near threshold distance is defined for avoiding that too much of a representation of a surface is incorrectly disregarded, since there may be noise in the representation and since the registration/alignment between representations or sub-scans may not be completely accurate. Reference numeral 1607 is the scan head of the scanner 1601, and reference numeral 1608 is the volume of the tooth.

The FIG. 20 is shown in 2D, but it is understood that the figure represents 3D figures.

Figure 17:
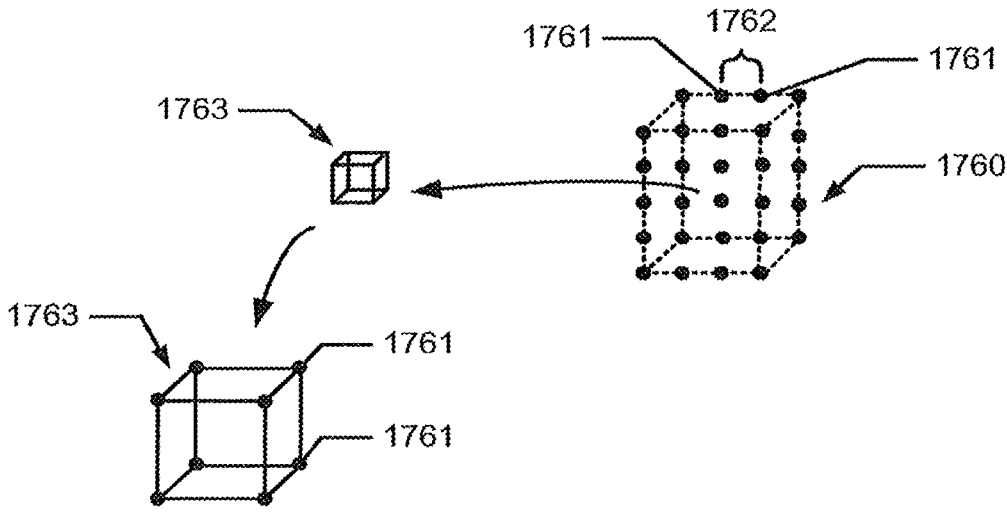
FIG. 17 shows an example of how the excluded volume is determined.

FIG. 17 shows an example of how the excluded volume is determined.

The space may be quantized in a 3D volume grid 1760. The distance 1762 between the corners 1761 in the 3D grid 1760 may be equidistant. The single cells 1763 in the grid each comprises eight corners 1761, and when each of the eight corners 1761 has been covered by a representation, then this cell 1763 is marked as seen. Thus if all eight corners 1761 of a cell 1763 is in the scan volume of a representation, then this cell 1763 may be marked as excluded volume. There may be such as ten, hundred, thousands or millions of cells in the space of a representation.

FIG. 18 shows examples of how movable objects can look in subscans.

Figure 18A:
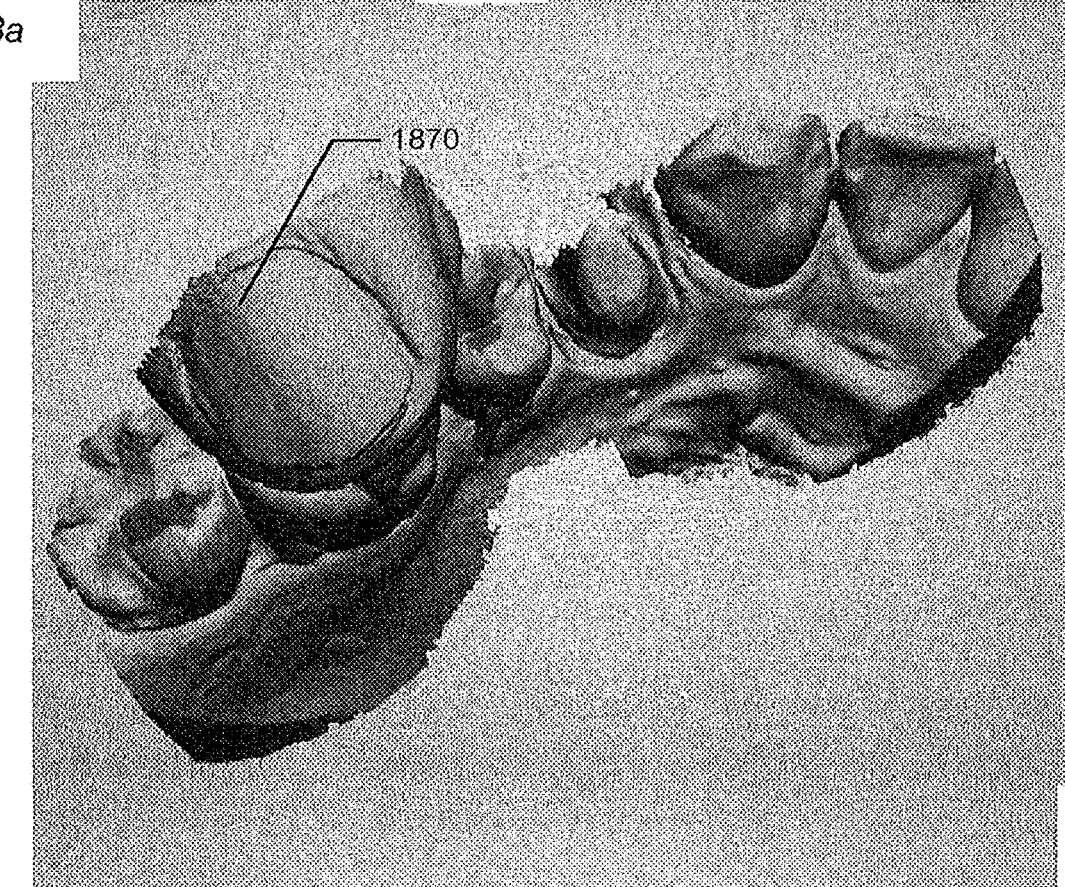
FIGS. 18*a* and 18*b* show examples of how movable objects can look in subscans.

FIG. 18a shows a subscan where the tip of a finger 1870 has been captured in the subscan.

Figure 18B:

FIG. 18b shows an example where a dental instrument 1871 has been captured in the subscan.

Figure 19:
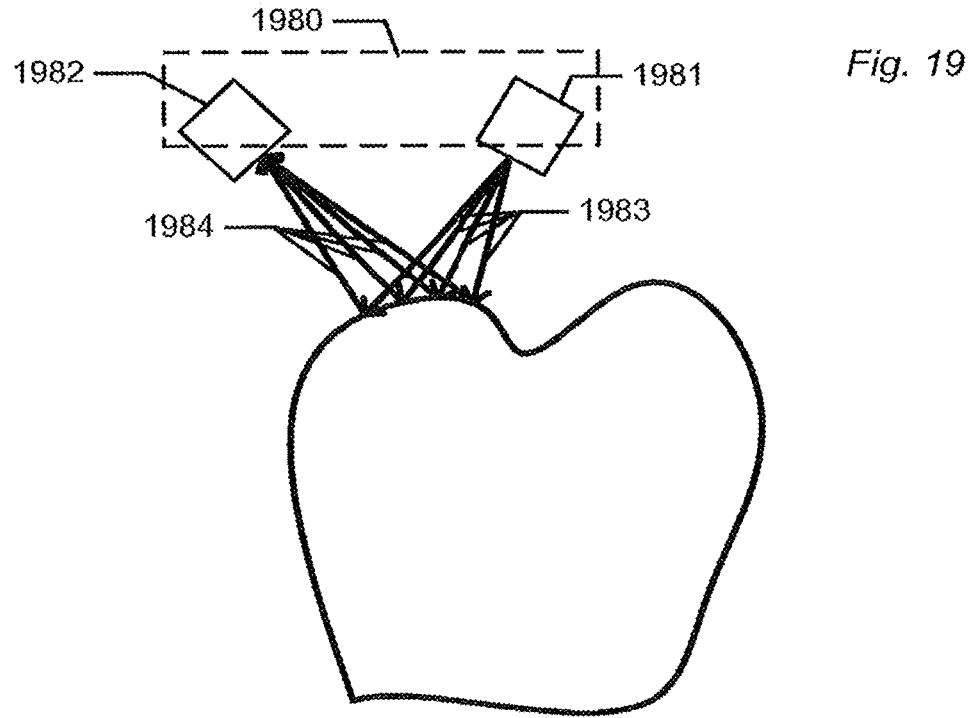
FIG. 19 shows an example of a pinhole scanner.

FIG. 19 shows an example of a pinhole scanner.

The pinhole scanner 1980 comprises a camera 1982 and a light source 1981, e.g. comprising a pattern (not shown). The light source 1981 transmits light rays 1983 to the surface 1916 from a small aperture, i.e. all the light rays 1983 transmitted to the surface 1961 are transmitted from a point. Light rays 1984 are reflected back from the surface 1961 and received by the camera 1982 through a small aperture.

Due to the pinhole setup, the point of light transmitted to the surface from the light source is well defined and the point of received light from the surface is also well defined.

Thus the excluded volume for a representation of the surface is defined by the volume in space that the light rays 1983 and 1984 span, and this volume is well defined due to the pinhole setup.

FIG. 20 shows examples of the principle of a far threshold distance from the captured surface defining a volume which is not included in the excluded volume of a representation.

The light rays 2052 (shown in dotted lines) from the scan head 2007 of the scanner 2001 may spread or scatter or disperse in any directions as seen in FIG. 20a, where a number of the light rays are illustrated. It is understood that only some of all the light rays are shown here. The surface area on the tooth surface where the light rays impinge has reference numeral 2016.

In FIG. 20b it is shown that even if an object 2072, such as a movable object, is arranged between the scan head 2007 and the surface 2016 of a tooth, the scanner 2001 may still capture a surface point 2053 on the tooth surface 2016 which is present or hidden "under" the object 2072, because of the angled or inclined light rays 2052. A surface point 2053 needs just be visible for one light ray from the scanner in order for that surface point to be detected.

Figure 20C:
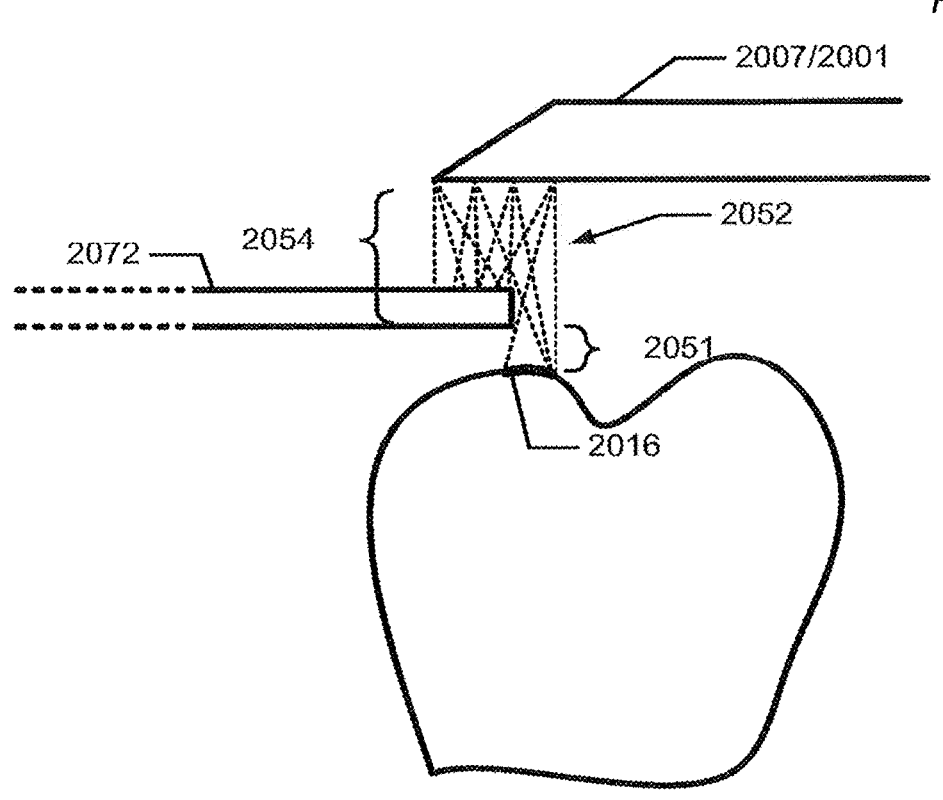

FIG. 20c shows an example of the far threshold distance 2051, which determines a distance from the captured surface 2016 in a representation, where any acquired data or surface or surface points, which is/are present or located outside the far threshold distance 2051, is not included in the excluded volume for the representation. Thus any acquired data or surface or surface points in the volume 2054 between the far threshold distance 2051 and the scan head 2007 is not used in defining the excluded volume of the representation.

Figure 20D:
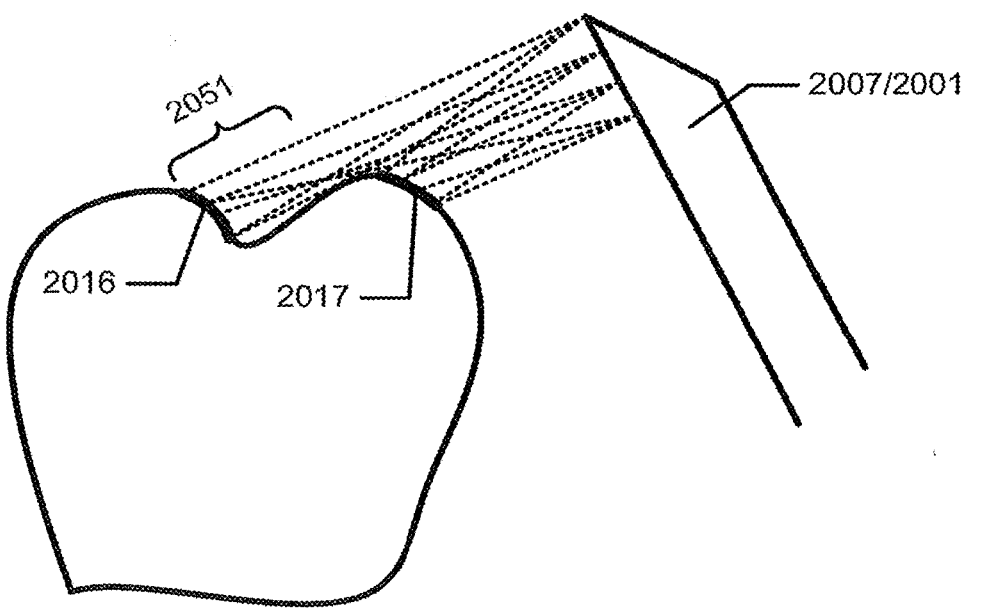

FIG. 20*d* shows an example where defining the far threshold distance is an advantage for avoiding that real tooth surface parts are erroneously disregarded.

The scanner 2001 should in principle capture all surface parts, 2016 and 2017, present in the scan volume, but in some cases the scanner cannot capture all surface parts in the scan volume. This may happen for example because the surface part is present outside the focus region of the scanner 2001 or of the scan head 2007 or because of poor lightning conditions for the surface part. In such cases the surface part 2017 may not be captured and registered, and an excluded volume would be determined in the space region where the surface part 2017 of the tooth surface is actually present. By defining the far threshold distance 2051 less of the scan volume is excluded, and thereby it can be avoided that a real surface part 2017 is erroneously disregarded.

The actual distance of the threshold may depend or be calculated based on the optics of the scanner. The far threshold distance may be a fixed number, such as about 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. Alternatively, the far threshold distance may be a percentage or a fraction of the length of the scan volume, such as about 20%, 25%, 30%, 35%, 40%, 45%, or 50% of the length of the scan volume, or such as ½, ⅓, ¼, ⅕ of the length of the scan volume.

The far threshold distance may be based on a determination of how far a distance from a detected point of the surface it is possible to scan, i.e. how much of the surface around a detected point that is visible for the scanner. If the visible distance in one direction from a surface point is short, then the far threshold distance will be smaller than if the distance in all directions from a surface point is long.

The figures in FIG. 20 are shown in 2D, but it is understood that the figures represent 3D figures.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for detecting movable objects recorded in subscans when scanning a set of teeth by means of an intraoral scanner for generating a virtual 3D model of the set of teeth, where the virtual 3D model is made up of a plurality of subscans of a surface of the set of teeth, and where new subscans are adapted to be added to the 3D virtual model when they are acquired, wherein the method comprises:

acquiring at least a first subscan of at least a first portion of the surface of the set of teeth, wherein a provisional virtual 3D model is initially defined by the at least first subscan;

determining a provisional excluded scan volume associated with the provisional virtual 3D model;

acquiring at least a second subscan of at least a second portion of the surface of the set of teeth, and defining the virtual 3D model based on the provisional virtual 3D model and any subsequent subscans including the second subscan;

determining an excluded scan volume associated with each of the subsequent subscans including the second subscan where no surface can be present in at least two of the subsequent scans;

determining an excluded scan volume of the virtual 3D model based on the provisional excluded scan volume and the excluded scan volumes associated with each of the subsequent subscans;

determining whether a surface of a movable object is present in the excluded scan volume of the virtual 3D model; and if the surface of the movable object is present in the excluded scan volume of the virtual 3D model, then disregard the surface of the movable object in the creation of the virtual 3D model of the set of teeth.

2. The method of claim 1, wherein the scanner is a handheld scanner.

3. The method of claim 1, wherein relative motion of the scanner and the set of teeth is determined.

4. The method of claim 1, wherein relative motion of the scanner and the set of teeth is determined by means of a motion sensor.

5. The method of claim 1, wherein the subscans are aligned/registered before a determination is made that a movable object is present.

6. The method of claim 1, wherein the scanner is an optical scanner and an optical system of the scanner is telecentric.

7. The method of claim 1, wherein the scanner is a pinhole scanner.

8. The method according to claim 1, wherein the movable object is one of:

a dentist's instrument which is temporarily present in a patient's mouth, a finger, and a soft tissue part of a patient's mouth.

9. The method according to claim 1, wherein at least part of the first portion of the surface of the set of teeth and at least part of the surface in the second subscan are overlapping a same surface part on the set of teeth.

* * * * *